(12) United States Patent
Hoveyda et al.

(10) Patent No.: US 10,787,458 B2
(45) Date of Patent: Sep. 29, 2020

(54) CHIRAL SYNTHESIS OF N-ACYL-(3-SUBSTITUTED)-(8-SUBSTITUTED)-5,6-DIHYDRO-[1,2,4]TRIAZOLO[4,3-A]PYRAZINES

(71) Applicant: OGEDA SA, Charleroi (BE)

(72) Inventors: Hamid Hoveyda, Brussels (BE); Guillaume Dutheuil, Vedrin (BE)

(73) Assignee: Ogeda SA, Brussels (BE)

( * ) Notice: Subject to any disclaimer, the term of this patent is extended or adjusted under 35 U.S.C. 154(b) by 0 days.

(21) Appl. No.: 16/361,737

(22) Filed: Mar. 22, 2019

(65) Prior Publication Data

US 2019/0218225 A1    Jul. 18, 2019

Related U.S. Application Data

(62) Division of application No. 15/512,919, filed as application No. PCT/EP2015/072167 on Sep. 25, 2015, now abandoned.

(30) Foreign Application Priority Data

Sep. 25, 2014 (EP) .................................... 14186447

(51) Int. Cl.
*C07D 487/04* (2006.01)
*C07D 241/08* (2006.01)

(52) U.S. Cl.
CPC ......... *C07D 487/04* (2013.01); *C07D 241/08* (2013.01)

(58) Field of Classification Search
CPC .................................................. C07D 487/04
See application file for complete search history.

(56) References Cited

U.S. PATENT DOCUMENTS

| 6,414,149 | B1 | 7/2002 | Chu-Moyer et al. |
| 8,871,761 | B2 | 10/2014 | Hoveyda et al. |
| 9,422,299 | B2 | 8/2016 | Hoveyda et al. |
| 9,475,814 | B2 | 10/2016 | Hoveyda et al. |
| 2007/0219181 | A1 | 9/2007 | Kimura et al. |
| 2012/0142672 | A1 | 6/2012 | Koike et al. |
| 2014/0371218 | A1 | 12/2014 | Hoveyda et al. |
| 2015/0315199 | A1 | 11/2015 | Hoveyda et al. |
| 2016/0289233 | A1 | 10/2016 | Hoveyda et al. |
| 2016/0304521 | A1 | 10/2016 | Hoveyda et al. |
| 2016/0318941 | A1 | 11/2016 | Hoveyda et al. |
| 2017/0029429 | A1 | 2/2017 | Hoveyda et al. |
| 2017/0095472 | A1 | 4/2017 | Hoveyda et al. |

FOREIGN PATENT DOCUMENTS

| JP | H06128261 A | 5/1994 |
| WO | 03/082817 A2 | 10/2003 |
| WO | 2004/014914 A1 | 2/2004 |
| WO | 2004/021984 A2 | 3/2004 |
| WO | 2004/080958 A2 | 9/2004 |
| WO | 2005/080397 A2 | 9/2005 |
| WO | 2009/089462 A1 | 7/2009 |
| WO | 2009/090055 A1 | 7/2009 |
| WO | 2010/125102 A1 | 11/2010 |
| WO | 2011/121137 A1 | 10/2011 |
| WO | 2013/050424 A1 | 4/2013 |

OTHER PUBLICATIONS

Nelson, et al. "1,2,4-Triazoles, VI.1 The Synthesis of Some s-Triazolo[4,3-1]pyrazines", Journal of Organic Chemistry, vol. 27, Sep. 1962, pp. 3243-3248.
Hansen, et al. "First Generation Process for the Preparation of the DPP-IV Inhibitor Sitagliptin", Organic Process Research & Development, vol. 9, No. 5, Aug. 2005, pp. 634-639.
Kowalchick, et al. "Design, Synthesis, and Biological Evaluation of Triazolopiperazine-Based Beta-Amino Amides as Potent, Orally Active Dipeptidyl Peptidase IV (DPP-4) Inhibitors", Bioorganic & Medicinal Chemistry Letters, vol. 17, Aug. 2007, pp. 5934-5939.
Balsells, et al. "Synthesis of [1,2,4]Triazolo[4,3-alpha]Piperazines Via Highly Reactive Chloromethyloxadiazoles", Organic Letters, vol. 7, No. 6, Feb. 2005, pp. 1039-1042.
McCort, et al. "A Rapid and Efficient Synthesis of Imidazo [1,2-a] and 1,2,4-Triazolo[4,3-a]-Piperazine Carboxylic Acids", Tetrahedron Letters, vol. 33, No. 31, Feb. 1992, pp. 4443-4446.
International Search Report issued in Application No. PCT/EP2015/072167, dated Oct. 30, 2015.
Registry (STN), [online], Feb. 14, 2014, [date of search Jul. 6, 2018], CAS Reg. No. 1544548-64-2.
Registry (STN), [online], Feb. 14, 2014, [date of search Jul. 6, 2018], CAS Reg. No. 1511418-10-1.
Registry (STN), [online], Feb. 14, 2014, [date of search Jul. 6, 2018], CAS Reg. No. 1544321-34-7.
Registry (STN), [online], Feb. 14, 2014, [date of search Jul. 6, 2018], CAS Reg. No. 1544321-11-0.
Registry (STN), [online], Feb. 14, 2014, [date of search Jul. 6, 2018], CAS Reg. No. 1544307-94-9.
Registry (STN), [online], Feb. 14, 2014, [date of search Jul. 6, 2018], CAS Reg. No. 1544205-03-9.

(Continued)

*Primary Examiner* — Brian E McDowell
(74) *Attorney, Agent, or Firm* — McCarter & English, LLP; Maria Laccotripe Zacharakis; Xin Zhang

(57) ABSTRACT

Disclosed is a novel chiral synthesis of N-acyl-(3-substituted)-(8-substituted)-5,6-dihydro-[1,2,4]triazolo[4,3-a] pyrazines of Formula (I):

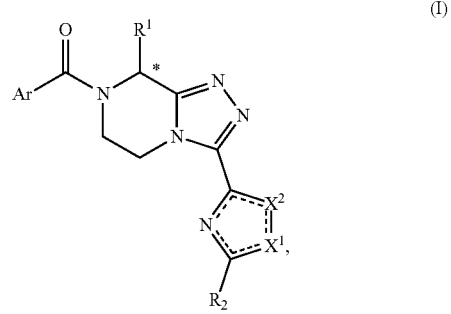

or a solvate thereof. The novel chiral synthesis avoids the use of protection/deprotection steps.

14 Claims, No Drawings

(56) References Cited

OTHER PUBLICATIONS

Registry (STN), [online], Feb. 14, 2014, [date of search Jul. 6, 2018], CAS Reg. No. 1544053-37-3.
Registry (STN), [online], Feb. 14, 2014, [date of search Jul. 6, 2018], CAS Reg. No. 1544048-36-3.
Registry (STN), [online], Feb. 14, 2014, [date of search Jul. 6, 2018], CAS Reg. No. 1543902-07-3.
Registry (STN), [online], Feb. 13, 2009, [date of search Jul. 6, 2018], CAS Reg. No. 1105699-61-3.
Japanese Office Action dated Sep. 4, 2018 in corresponding Japanese Patent Application No. 2017-516089 with JPO machine translation of Japanese Office Action.

CHIRAL SYNTHESIS OF N-ACYL-(3-SUBSTITUTED)-(8-SUBSTITUTED)-5,6-DIHYDRO-[1,2,4]TRIAZOLO[4,3-A]PYRAZINES

FIELD OF INVENTION

The present invention relates to a novel chiral synthesis of N-acyl-(3-substituted)-(8-substituted)-5,6-dihydro-[1,2,4]triazolo[4,3-a]pyrazines of Formula I, avoiding the use of protection/deprotection steps.

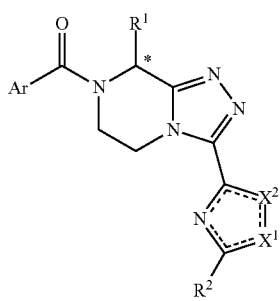

BACKGROUND OF INVENTION

The synthesis of N-acyl-(3-substituted)-(8-substituted)-5,6-dihydro-[1,2,4]triazolo[4,3-a]pyrazines is disclosed in the literature, comprising a) the synthesis of (3-substituted)-(8-substituted)-5,6-dihydro-[1,2,4]triazolo[4,3-a]pyrazine intermediates, followed by b) a classical N-acylation (Scheme 1):

Scheme 1: General synthetic scheme for the preparation of N-acyl-(3-substituted)-(8-substituted)-5,6-dihydro-[1,2,4]triazolo[4,3-a]pyrazines according to the prior art.

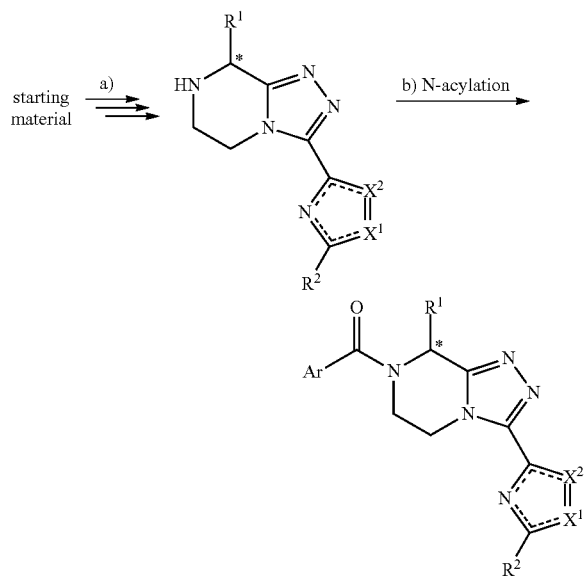

Different synthetic approaches that are of general relevance to step a) of the synthesis of chiral (3-substituted)-(8-substituted)-5,6-dihydro-[1,2,4]triazolo[4,3-a]pyrazine intermediates are known in the literature. The below examples and experimental conditions of relevant approaches provided are illustrative only.

In Method A(i) (see Scheme 2), the [1,2,4]triazolopyrazine core IIIa(i) is formed by acetylation of 2-hydrazidopyrazine (step 1) followed by a cyclodehydration reaction (step 2), using procedures familiar to those skilled in the art. This methodology was initially developed by Nelson and Potts (*J. Org. Chem.* 1962, 27, 3243-3248). Subsequent reduction of the pyrazine ring with $H_2$/Pd affords the [1,2,4]triazolo[4,3-a]piperazine (step 3). This method is well described in the literature and has been used, for example, in the Merck synthesis of Sitagliptin (Hansen et al., *Org. Process Res. Dev.* 2005, 9, 634-639 and references therein).

Scheme 2: Method A(i).

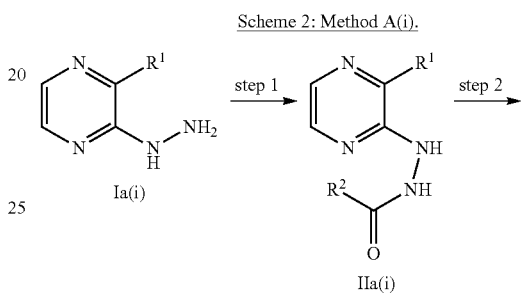

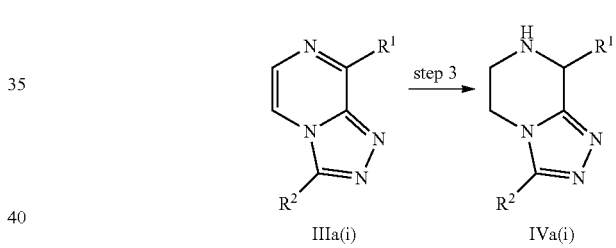

However, i) perusal of the existing literature indicates that this procedure is generally used with substrates wherein $R^1$=H (i.e. non-chiral analogs, cf. Scheme 2), and ii) that the application of this method to prepare chiral [1,2,4]triazolo[4,3-a]piperazine variant of general Formula IVa(i) (in Method A(i)) has not been disclosed. The dearth of examples of pyrazine substrates wherein $R^1 \neq H$ in this methodology may be due to the difficulty of pyrazine reduction step; noteworthy in this regard is the fact that in the optimized process scale-up procedure reported by Hansen et al., the pyrazine ($R^1$=H) reduction (step 3, Scheme 2) proceeded in merely 51% yield. In addition to the issue of chemical yield, access to chiral substrates through reduction of [1,2,4]triazolopyrazine substrates wherein $R^1 \neq H$ would require the additional challenge of efficient asymmetric hydrogenation conditions (in terms of both yield and chiral purity); this is currently not a known procedure to the best of Applicant's knowledge. Thus application of Method A(i) for chiral synthesis of [1,2,4]triazolo[4,3-a]piperazine structures is hitherto unknown.

Method A(ii) (cf. Scheme 3) is a variation on Method A(i) whereby the reduction of $R^1 \neq H$ substituted [1,2,4]triazolopyrazine substrates is circumvented.

Scheme 3: Method A(ii).

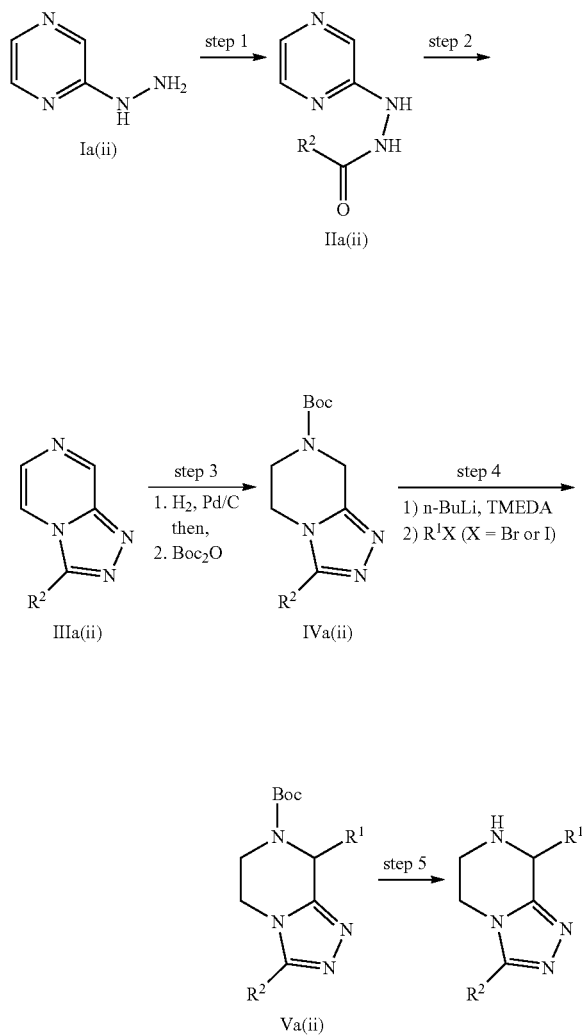

Scheme 4: Method B.

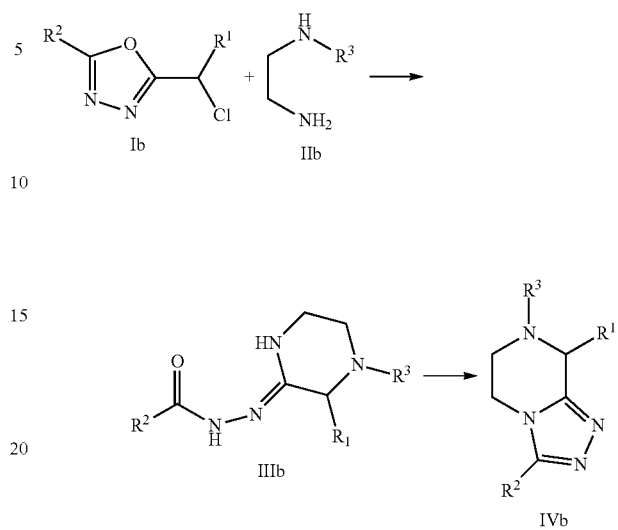

As reported by Balsells et al., however, this approach proceeds in high yield mainly when the strong electron-withdrawing $R^2$=$CF_3$ group is present in the chloromethyloxadiazole reagent. In addition, the mechanism suggested by the said authors would render application of this strategy unlikely, if not impossible, for a chiral synthesis of IVb intermediates (cf. Scheme 4). Indeed, in the current literature only racemic or achiral products are described using such an approach. Thus, application of Method B towards preparation of chiral [1,2,4]triazolo[4,3-a]piperazine structures has never been disclosed.

Another well-known method for the preparation of [1,2,4]triazolo[4,3-a]piperazine containing structures is shown in Scheme 5 below (Method C).

This method has been reported by the Merck group in their studies related to Sitagliptin (see, for example, Kowalchick et al., *Bioorg. Med. Chem. Lett.* 2007, 17, 5934-5939), wherein Boc-protected intermediates depicted by general Formula IVa(ii) are deprotonated with a strong base, such as n-butyllithium, in the presence of tetramethylethylenediamine (TMEDA), followed by treatment of the thus generated anion with an electrophile such as an alkyl halide (step 4, Scheme 3). The chiral variant of this methodology has not been reported in the literature.

Inspired by the earlier work by Makino and Kato (JPH06128261(A), 1994), yet another alternative approach to the synthesis of [1,2,4]triazolo[4,3-a]piperazines was developed using chloromethyloxadiazoles as a key reagent (Balsells et al., *Org. Lett.* 2005, 7, 1039-1042). This methodology (Method B) is depicted in Scheme 4 below.

Scheme 5: Method C.

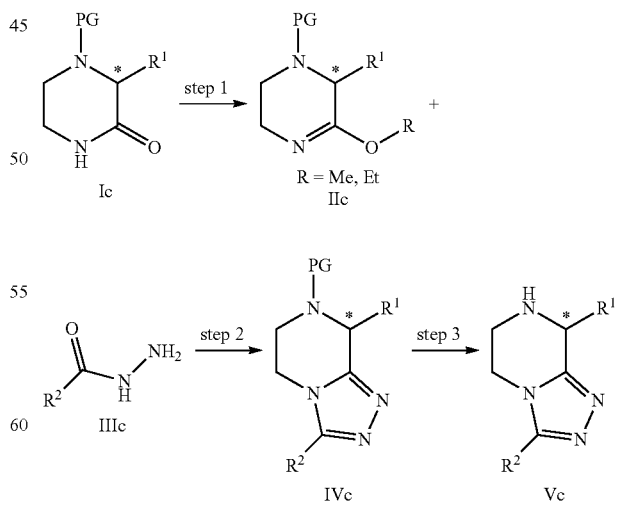

The symbol * denotes a well-defined configuration at the carbon center next to which the said symbol is placed, i.e. the carbon atom to which the $R^1$ group is attached in this scheme.

Addition of acetylhydrazide to piperazinoimidate (step 1) is followed by cyclodehydration to form the fused triazolo ring (step 2). This method is well documented in the literature although exemplified only through racemic or achiral structures; e.g.: McCort and Pascal, *Tetrahedron Lett.*, 1992, 33, 4443-4446; Brockunier et al. WO 03/082817 A2; Chu-Moyer et al. U.S. Pat. No. 6,414,149 B1; Banka et al. WO2009/089462 A1. To the best of his knowledge, the Applicant is unaware of any published reports of the application of this method for obtaining chiral products by starting from chiral piperazinones (Ic in Scheme 5).

A synthesis of (R)-8-methyl-5,6,7,8-tetrahydro-[1,2,4]triazolo[4,3-a]pyrazine compounds through general Method C has been previously described in international patent application WO2011/121137 which is in the name of the Applicant. The preparation disclosed therein is depicted in Scheme 6:

with the preparation of pharmaceutically active ingredient, for instance. Step 2 is the piperazinoimidate formation (i.e., 1.2→1.3) and step 3 is the cyclodehydration step between the said imidate and acetylhydrazide (i.e., 1.3+1.4→1.5).

An important disadvantage of the Scheme 6 procedure is that racemization of the stereogenic carbon center occurred frequently in steps 2-3. Consequently, the said procedure furnished final products that were only infrequently of acceptable chiral purity; in fact, much more frequently, the Scheme 6 procedures produced final products represented by the general Formula 1.7 in what is considered essentially racemic by those skilled in the art. As such, said method cannot be used in practice to prepare a pharmaceutically active ingredient as this method does not reliably furnish chiral intermediates (1.3, 1.5, 1.6; Scheme 6) and thus cannot be reliably used for obtaining chiral products represented by the general Formula 1.7.

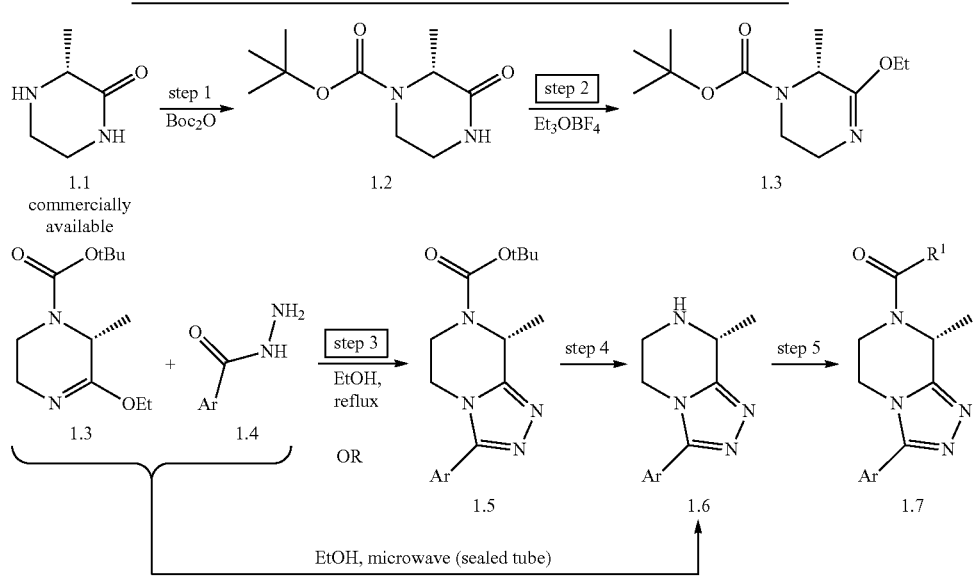

Scheme 6: Synthesis of (R)-8-methyl-5,6,7,8-tetrahydro-[1,2,4]triazolo[4,3-a]pyrazine intermediates according to WO2011/121137.

Note: Steps 2 and 3 are particularly prone to racemization despite the graphic depiction of chiral products for each of these steps in the above scheme. Thus, obtaining intermediates/products in high chiral purity (>80% ee) is feasible but not in a reproducible fashion.

Boc-protected ketopiperazine 1.2 was prepared and then converted to iminoether 1.3 by using the Meerwein reagent (e.g. $Et_3OBF_4$). Cyclodehydration reaction between the acyl hydrazide 1.4 and the iminoether aforementioned was conducted either under forcing thermal reflux conditions, or by applying excessive microwave irradiation in a sealed tube typically for rather protracted reaction times (often days). When using microwave irradiation, N-Boc deprotection occurred during the said cyclodehydration step; thus, a deprotection step was typically not necessary to conduct (i.e., 1.3+1.4→1.6 in Scheme 6). However, when thermal cyclodehydration conditions were applied, Boc-deprotection step was required (i.e., 1.3+1.4→1.5→1.6).

As noted in Scheme 6 above, steps 2 and 3 have shortcomings that significantly limit the application of the said procedure for uses wherein generation of chiral intermediates or products are required in a reproducible fashion, as Another disadvantage of the Scheme 6 procedure is the excessively protracted reaction time required for the cyclodehydration step (Scheme 6, 1.3+1.4→1.5). Up to several days (under forcing reaction conditions—see below) were always required with substrates represented by the general Formula IIc (Scheme 5) wherein R≠H, i.e. the more sterically congested analogs, unlike the case with achiral substrates represented by the general Formula IIc (Scheme 5) wherein R=H. Such significantly protracted reaction times (several days) are not practical for such cases as a cGMP scale-up synthesis required to prepare a pharmaceutically active ingredient for clinical studies.

As adumbrated in the above paragraph, in the Scheme 6 procedure, the cyclodehydration step required extremely forcing conditions. Thus, use of elevated temperatures at reflux (for protracted durations), or additionally with application of essentially maximally feasible (within margin of experimental safety) microwave irradiation (sealed vessel) were often required.

Applicant resorted to a racemic synthesis from racemic 5,6,7,(8-methyl)-tetrahydro-[1,2,4]triazolo[4,3-a]pyrazine followed by an additional chiral preparative HPLC purification step after forming the final product of interest depicted by the general Formula 1.7 in Scheme 6. While feasible on small scale for the initial research and development phase, such an approach poses the problems of scalability in terms of time, cost and general applicability to such needs as cGMP scale-up of a pharmaceutically active ingredients, for instance.

An improved chiral synthesis of 5,6,7,(8-substituted)-tetrahydro-[1,2,4]triazolo[4,3-a]pyrazine intermediates has then been described in international patent application WO2013/050424 which is in the name of the Applicant.

This method is a variation on the method depicted in Scheme 6: the Boc protective group of Scheme 6, which is a N-Csp² protective group, was replaced by a N-Csp³ protective group, preferably a benzylic protective group such as DMB, PMB or TMB.

The use of such a N-Csp³ protective group was observed to provide 5,6,7,(8-substituted)-tetrahydro-[1,2,4]triazolo[4,3-a]pyrazine chiral intermediates with a good enantiomeric excess and in a reproducible fashion. Retention of stereochemistry was observed with minimal if any racemization.

Even though the method described in WO2013/050424 enables chiral synthesis of N-acyl-(3-substituted)-(8-substituted)-5,6-dihydro-[1,2,4]triazolo[4,3-a]pyrazines, the Applicant conducted research to further improve the process, especially its scalability in terms of time, cost, number of steps, while minimizing racemization. This is all the more important as these compounds are useful as selective antagonists to neurokinin 3 receptor (NK-3) thereby making such improved synthetic procedure of practical utility towards development of such products as pharmaceutical active ingredients.

In contrast to all previously described methods, the new chiral synthetic procedure of the present invention first involves an N-acylation step followed by the building of the [1,2,4]triazolo[4,3-a]pyrazine core (Scheme 7):

Scheme 7: General synthetic scheme for the preparation of N-acyl-(3-substituted)-(8-substituted)-5,6-dihydro-[1,2,4]triazolo[4,3-a]pyrazines of the invention.

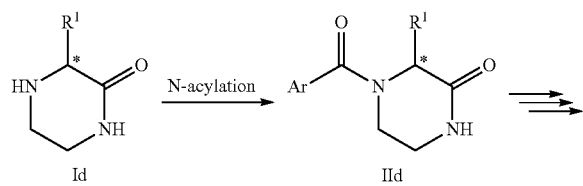

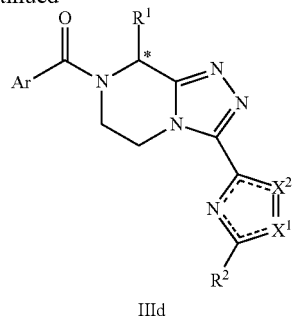

This strategy, while described for the synthesis of non-chiral substrates (i.e. $R^1$=H) by Glaxo Group Limited (WO 2010/125102 A1), was never applied to the chiral synthesis of N-acyl-(3-substituted)-(8-substituted)-5,6-dihydro-[1,2,4]triazolo[4,3-a]pyrazines. As explained above for the method of Scheme 6, protection of the amine nitrogen atom with Boc N-Csp² protective group (such as N-Boc) frequently resulted in impractically high levels of racemization under the previously reported conditions. Despite the aforesaid earlier findings, further efforts revealed that with more rigorously controlled milder experimental conditions (lower temperature and shorter reaction time), presence of specific N-Csp² groups, such as N-Boc protective group or N-benzoyl substitution, can still result in final products with acceptably low (<5%) racemization. However these latter findings were also contingent upon the nature of the 5-membered heterocyclic ring in such a way that it can be of practical value to the target structures of interest by the Applicant as antagonists to the neurokinin-3 receptor. Collectively the aforementioned results are unexpected for those skilled in the art.

Therefore, the new synthetic procedure of the present invention presents the distinct advantage of furnishing final desired targets with very high chiral purity while obviating the need of additional protection/deprotection steps that will advantageously impact production costs.

SUMMARY

The invention relates to a process of preparing chiral N-acyl-(3-substituted)-(8-substituted)-5,6-dihydro-[1,2,4]triazolo[4,3-a]pyrazine of general Formula I:

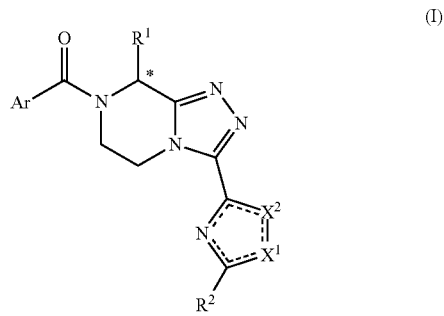

or solvates thereof, wherein
$R^1$ is alkyl, haloalkyl, hydroxyalkyl or alkoxyalkyl, preferably $R^1$ is methyl, ethyl, n-propyl, hydroxyethyl, methoxyethyl, trifluoromethyl, difluoromethyl or fluoromethyl; more preferably $R^1$ is methyl;

$R^2$ is alkyl, alkoxyalkyl or haloalkyl, preferably $R^2$ is methyl, ethyl, methoxymethyl, trifluoromethyl, difluoromethyl, fluoromethyl, 1-fluoroethyl, 1,1-difluoroethyl or 2,2,2-trifluoroethyl; more preferably $R^2$ is methyl, ethyl, methoxymethyl, trifluoromethyl, difluoromethyl or fluoromethyl; even more preferably $R^2$ is methyl;

Ar is a phenyl group, optionally substituted by one or more substituent(s) selected from H, halo, alkyl, alkoxy, haloalkyl, nitrile and thiophen-2-yl; preferably Ar is a phenyl group, optionally substituted by one or more substituent(s) selected from H, F, Cl, methyl, methoxy, trifluoromethyl, nitrile and thiophen-2-yl; more preferably Ar is a phenyl group substituted by H or F;

$X^1$ is N and $X^2$ is S or O; or $X^1$ is S and $X^2$ is N;

=== represents a single or a double bound depending on $X^1$ and $X^2$;

said process comprising the following steps:

a) reacting a compound of Formula A:

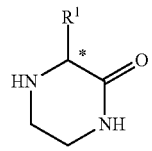

(A)

wherein $R^1$ is as defined above;
with a compound of Formula B:

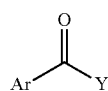

(B)

wherein Ar is as defined above; and Y is hydroxyl or halo, wherein halo is preferably F or Cl; more preferably Y is hydroxyl or Cl, even more preferably Y is Cl;
to obtain a compound of Formula C:

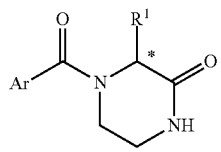

(C)

b) converting the compound of Formula C with a tri(C1-C2 alkyl)oxonium salt, a (C1-C2)alkylsulfate, a (C1-C2) chloroformate or $PCl_5/POCl_3/$(C1-C2)hydroxyalkyl, so as to obtain a compound of Formula D:

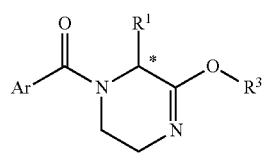

(D)

wherein Ar and $R^1$ are as defined above, and $R^3$ is C1-C2 alkyl;
in the presence of a base;

c) reacting the compound of Formula D with a compound of Formula E:

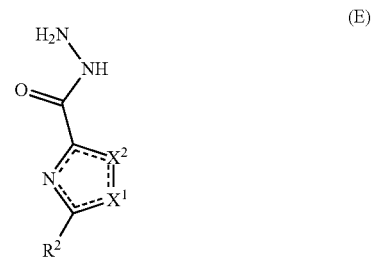

(E)

or a salt or solvate thereof, wherein $X^1$, $X^2$ and $R^2$ are as defined above;

so as to obtain a compound of Formula I or solvate thereof.

According to the present invention, the reaction of each step is carried out under controlled mild experimental conditions. Especially, the reaction is carried out at a temperature equal to or below boiling point of the organic solvent, preferably at room temperature.

In one embodiment, the process does not use any protecting group.

In one embodiment, the process proceeds with the retention of stereochemistry with respect to the starting material.

The process according to the present invention preferably provides the (R)-enantiomer of compounds of Formula I.

The invention also refers to synthesis of chiral intermediates.

In one embodiment, the process provides chiral compounds of Formula C:

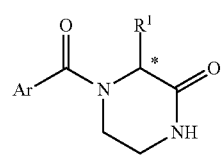

(C)

or solvates thereof, wherein $R^1$ and Ar are as defined above.

In one preferred embodiment, compound C has Formula C-b2:

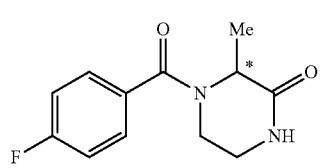

(C-b2)

The invention also refers to compounds of Formula D:

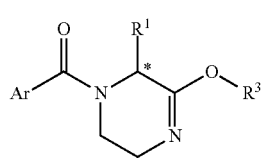

or solvates thereof, wherein $R^1$, $R^3$ and Ar are as defined above.

In one preferred embodiment, compound D has Formula D-1:

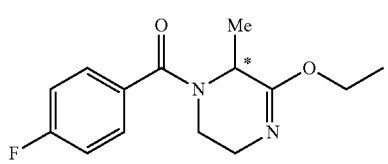

Preferred compounds of Formula C and Formula D are those wherein the stereoisomer obtained is the (R)-enantiomer.

The invention also relates to the use of the compounds provided by the process or solvate thereof, for the manufacture of a medicament, a pharmaceutical composition or a pharmaceutically active ingredient.

DETAILED DESCRIPTION

Process

The invention relates to a novel chiral synthesis of N-acyl-(3-substituted)-(8-substituted)-5,6-dihydro-[1,2,4]triazolo[4,3-a]pyrazine compounds avoiding use of protection/deprotection steps and thus, allowing achieving high chiral purity while improving cost-effectiveness. Especially, the invention relates to a process of preparing N-acyl-(3-substituted)-(8-substituted)-5,6-dihydro-[1,2,4]triazolo[4,3-a]pyrazine compounds of Formula I:

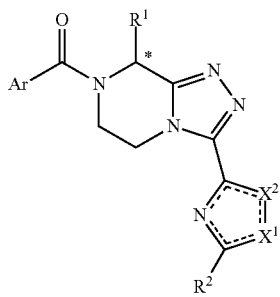

or solvates thereof, wherein $R^1$ is alkyl, haloalkyl, hydroxyalkyl or alkoxyalkyl, preferably $R^1$ is methyl, ethyl, n-propyl, hydroxyethyl, methoxyethyl, trifluoromethyl, difluoromethyl or fluoromethyl; more preferably $R^1$ is methyl;

$R^2$ is alkyl, alkoxyalkyl or haloalkyl, preferably $R^2$ is methyl, ethyl, methoxymethyl, trifluoromethyl, difluoromethyl, fluoromethyl, 1-fluoroethyl, 1,1-difluoroethyl or 2,2,2-trifluoroethyl; more preferably $R^2$ is methyl, ethyl, methoxymethyl, trifluoromethyl, difluoromethyl or fluoromethyl; even more preferably $R^2$ is methyl;

Ar is a phenyl group, optionally substituted by one or more substituent(s) selected from H, halo, alkyl, alkoxy, haloalkyl, nitrile and thiophen-2-yl; preferably Ar is a phenyl group, optionally substituted by one or more substituent(s) selected from H, F, Cl, methyl, methoxy, trifluoromethyl, nitrile and thiophen-2-yl; more preferably Ar is a phenyl group substituted by H or F;

$X^1$ is N and $X^2$ is S or O; or $X^1$ is S and $X^2$ is N;

⹀ represents a single or a double bound depending on $X^1$ and $X^2$;

said process comprising the following steps:

a) reacting a compound of Formula A:

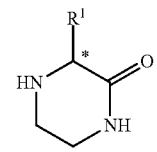

wherein $R^1$ is as defined above;

with a compound of Formula B:

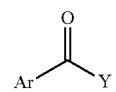

wherein Ar is as defined above; and Y is hydroxyl or halo, wherein halo is preferably F or Cl; more preferably Y is hydroxyl or Cl, even more preferably Y is Cl;

to obtain a compound of Formula C:

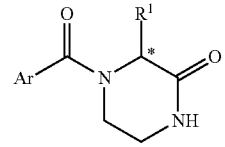

b) converting the compound of Formula C with a tri(C1-C2 alkyl)oxonium salt, a (C1-C2)alkylsulfate, a (C1-C2) chloroformate or $PCl_5/POCl_3$/(C1-C2)hydroxyalkyl, so as to obtain a compound of Formula D:

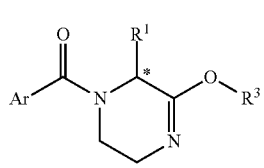

wherein Ar and $R^1$ are as defined above, and $R^3$ is C1-C2 alkyl;
in the presence of a base;
c) reacting the compound of Formula D with a compound of Formula E:

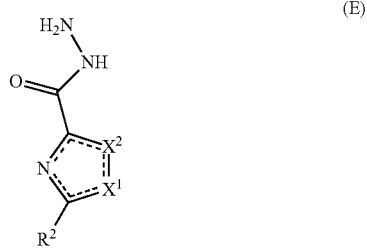

or a salt or solvate thereof, wherein $X^1$, $X^2$ and $R^2$ are as defined above; so as to obtain a compound of Formula I or solvate thereof.

The below description of the process of the invention applies to the process of the invention as defined above, including all embodiments described.

According to a first embodiment, the process is carried out under controlled mild experimental conditions.

Amide coupling step a) of the process as defined above is advantageously carried out in an organic, preferably anhydrous, solvent, selected from dichloromethane, acetonitrile preferably in dichloromethane.

The reaction is advantageously carried out at a temperature equal to or below boiling point of the organic solvent, preferably at room temperature.

The term "room temperature" as used herein means a temperature comprised between 10° C. and 30° C., preferably 20±5° C.

In the case of compounds of Formula B wherein Y is a halo, the reaction is carried out in the presence of a base selected from the group consisting of di-iso-propylethylamine, N-methylmorpholine, triethylamine, preferably N-methylmorpholine. In the case of compounds of Formula B wherein Y is a hydroxyl, the reaction is carried out on an activated anhydride, ester, acylurea derivative of the latter said compounds—formed through conventional amide bond forming reagent(s) involving the use of so-called activating groups, such as isobutylchloroformate, DIC, DCC, HOBt, HATU, HBTU, DEPBT under reaction conditions known to those skilled in the art. According to a preferred embodiment, Y is a halo in compounds of Formula B and the reaction is carried out in the presence of a base selected from the group consisting of di-iso-propylethylamine, N-methylmorpholine, triethylamine, preferably N-methylmorpholine.

Intermediates of Formula C may be optionally purified by silica gel flash chromatography or silica gel chromatography, and/or precipitation, and/or trituration, and/or filtration, and/or recrystallization.

The second step of the process, step b), is the conversion of the ketopiperazine compounds of Formula C to iminoether compounds of Formula D.

Step b) proceeds without significant loss of chirality resulting in the corresponding products of good enantiomeric purity as defined herein.

The procedure involves a tri(C1-C2 alkyl)oxonium salt (Meerwein-type reagents), or (C1-C2)alkylsulfate, or (C1-C2)chloroformate, or use of $PCl_5/POCl_3$/(C1-C2)hydroxyalkyl, preferably tri(C1-C2 alkyl)oxonium salt (Meerwein-type reagents), or (C1-C2)alkylsulfate, more preferably tri (C1-C2 alkyl)oxonium salt, and even more preferably a tri(C2 alkyl)oxonium salt, such as $Et_3OBF_4$.

As set out above, step b) is carried out in the presence of a base.

Use of at least 2 equivalents of tri(C1-C2 alkyl)oxonium salt with respect to the 3-substituted-piperazin-2-one of Formula C was required to aid towards a more complete conversion when step b) was carried out without a mild base additive, such as $Na_2CO_3$, as further discussed hereunder.

Without being bound by any theory, Applicant believes that formation of an acid such as $HBF_4$ may be a sideproduct with the use of moisture-sensitive tri(C1-C2 alkyl) oxonium salt (Meerwein-type reagents). Interestingly, there exist two literature references (See (a) Sánchez et al., *J. Org. Chem.* 2001, 66, 5731-5735; (b) Kende et al., *Org. Lett.* 2003, 5, 3205-3208) that cite the use of mild bases such as $Na_2CO_3$ in conjunction with the use of Meerwein reagent although i) without offering any explicit rationale or detailed experimental conditions. After extensive reaction optimization experiments, Applicant found that addition of a base, especially $Na_2CO_3$, with respect to the Meerwein reagent helped minimize racemization. Applicant further observed that use of a mild base additive, especially $Na_2CO_3$, appears to also help accelerate the reaction towards completion that in turn may contribute to minimizing racemization in such reactions.

The base is advantageously selected from the group consisting of sodium carbonate, sodium bicarbonate, potassium carbonate or cesium carbonate, preferably the base is sodium carbonate.

In a preferred embodiment, between 1 and 5, preferably about 1.8 mole equivalents with respect to tri(C1-C2 alkyl) oxonium salt of base are used.

The tri(C1-C2 alkyl)oxonium salt is advantageously selected from the group consisting of trimethyloxonium tetrafluoroborate, triethyloxonium tetrafluoroborate, preferably the tri(C1-C2 alkyl) oxonium salt is triethyloxonium tetrafluoroborate. In an advantageous embodiment, between 1 and 2, preferably about 1.25, mole equivalents of tri(C1-C2 alkyl)oxonium salt is used, with respect to the 3-substituted-piperazin-2-one.

The iminoether synthesis step b) is advantageously carried out in an organic, preferably anhydrous, solvent, preferably dichloromethane.

The reaction is advantageously carried out at a temperature equal to or below the boiling point of the organic solvent; preferably the reaction is carried out at room temperature.

Intermediates of Formula D may optionally be purified by flash or column chromatography on silica gel.

The third step of the process, step c), is the preparation of triazolopiperazine compounds of Formula I by condensation between an iminoether of Formula D and an acylhydrazide of Formula E or a salt or solvate thereof.

Step c) is generally carried out at a temperature comprised between 50° C. and 135° C., preferably between 50° C. and 90° C.; more preferably the temperature is about 70° C.

Compounds of Formula I may optionally be purified by silica gel flash chromatography or silica gel chromatography, and/or precipitation, and/or trituration, and/or filtration, and/or recrystallization.

The process of the invention provides compounds of Formula I or solvate thereof having good enantiomeric excess of up to 97% and possibly more in a reproducible fashion.

The process of the invention proceeds with the retention of stereochemistry with respect to the starting material except to the extent that racemization occurs as a minor side-reaction; thus the configuration at position 8 of the ring is defined by the configuration of the aforesaid chiral starting material.

According to an advantageous embodiment, through the use of chiral 3-substituted-piperazin-2-one starting material, the process of the invention provides access to N-acyl-(3-substituted)-(8-substituted)-5,6-dihydro-[1,2,4]triazolo[4,3-a]pyrazines by minimizing any intervening racemization during the process.

Compounds of Formula I

The process of invention provides compounds of Formula I; preferably said compounds are the (R)-enantiomer.

According to the present invention, preferred compounds of Formula I are those of Formula I':

(I')

and pharmaceutically acceptable solvates thereof, wherein $R^1$ is alkyl, haloalkyl, hydroxyalkyl or alkoxyalkyl, preferably $R^1$ is methyl, ethyl, n-propyl, hydroxyethyl, methoxyethyl, trifluoromethyl, difluoromethyl or fluoromethyl; more preferably $R^1$ is methyl;

$R^2$ is alkyl, alkoxyalkyl or haloalkyl, preferably $R^2$ is methyl, ethyl, methoxymethyl, trifluoromethyl, difluoromethyl, fluoromethyl, 1-fluoroethyl, 1,1-difluoroethyl or 2,2,2-trifluoroethyl; more preferably $R^2$ is methyl, ethyl, methoxymethyl, trifluoromethyl, difluoromethyl or fluoromethyl; even more preferably $R^2$ is methyl;

$R_a$ $R_{a'}$, $R_b$, $R_{b'}$ and $R_c$ represent independently H, halo, alkyl, alkoxy, haloalkyl, nitrile or thiophen-2-yl; preferably H, F, Cl, methyl, methoxy, trifluoromethyl, nitrile or thiophen-2-yl; more preferably H or F;

$X^1$ is N and $X^2$ is S or O; or $X^1$ is S and $X^2$ is N.

In one embodiment, preferred compounds of Formula I are those of Formula Ia:

(Ia)

and pharmaceutically acceptable solvates thereof, wherein $R^1$, $R^2$, $R_a$, $R_{a'}$, $R_b$, $R_{b'}$ and $R_c$ are as defined above.

In one embodiment, preferred compounds of Formula Ia are those of Formula Ia':

(Ia')

and pharmaceutically acceptable solvates thereof, wherein $R^1$ is alkyl, haloalkyl, hydroxyalkyl or alkoxyalkyl, preferably $R^1$ is methyl, ethyl, n-propyl, hydroxyethyl, methoxyethyl, trifluoromethyl, difluoromethyl or fluoromethyl; more preferably $R^1$ is methyl;

$R^2$ is alkyl, alkoxyalkyl or haloalkyl, preferably $R^2$ is methyl, ethyl, methoxymethyl, trifluoromethyl, difluoromethyl, fluoromethyl, 1-fluoroethyl, 1,1-difluoroethyl or 2,2,2-trifluoroethyl; more preferably $R^2$ is methyl, ethyl, methoxymethyl, trifluoromethyl, difluoromethyl or fluoromethyl; even more preferably $R^2$ is methyl;

$R_a$ $R_{a'}$, $R_b$, $R_{b'}$ and $R_c$ represent independently H, halo, alkyl, alkoxy, haloalkyl, nitrile or thiophen-2-yl; preferably H, F, Cl, methyl, methoxy, trifluoromethyl, nitrile or thiophen-2-yl; more preferably H or F.

According to one embodiment, preferred compounds of Formula Ia and Ia' and pharmaceutically acceptable solvates thereof are those wherein:

$R^1$ is methyl, ethyl, n-propyl, hydroxyethyl, methoxyethyl, trifluoromethyl, difluoromethyl or fluoromethyl; preferably $R^1$ is methyl;

$R^2$ is methyl, ethyl, methoxymethyl, trifluoromethyl, difluoromethyl, fluoromethyl, 1-fluoroethyl, 1,1-difluoroethyl or 2,2,2-trifluoroethyl; preferably $R^2$ is methyl, ethyl, methoxymethyl, trifluoromethyl, difluoromethyl or fluoromethyl; more preferably $R^2$ is methyl;

$R_a$ is H, F or methyl;

$R_{a'}$ is H;

$R_b$ is H, F, Cl or methoxy;

$R_{b'}$ is H or F; and $R_c$ is H, F, Cl, methyl, trifluoromethyl or nitrile.

In one embodiment, preferred compounds of Formula I are those of Formula Ia-1:

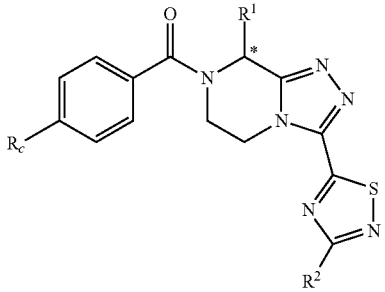

(Ia-1)

and pharmaceutically acceptable solvates thereof, wherein:

$R_c$ is H, F, Cl, methyl, trifluoromethyl or nitrile; preferably $R_c$ is H, F or Cl;

$R^1$ is alkyl, haloalkyl, hydroxyalkyl or alkoxyalkyl, preferably $R^1$ is methyl, ethyl, n-propyl, hydroxyethyl, methoxyethyl, trifluoromethyl, difluoromethyl or fluoromethyl; more preferably $R^1$ is methyl; and $R^2$ is alkyl, alkoxyalkyl or haloalkyl, preferably $R^2$ is methyl, ethyl, methoxymethyl, trifluoromethyl, difluoromethyl, fluoromethyl, 1-fluoroethyl, 1,1-difluoroethyl or 2,2,2-trifluoroethyl; more preferably $R^2$ is methyl, ethyl, methoxymethyl, trifluoromethyl, difluoromethyl or fluoromethyl; even more preferably $R^2$ is methyl.

In one embodiment, preferred compounds of Formula Ia-1 are those of Formula Ia-1':

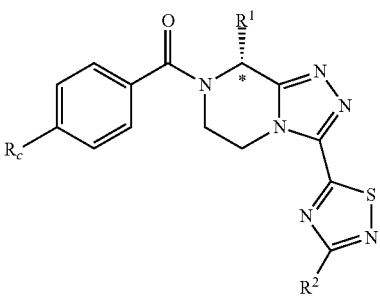

(Ia-1')

and pharmaceutically acceptable solvates thereof, wherein:

$R^1$, $R^2$ and $R_c$ are as defined in Formula Ia-1.

In one embodiment, preferred compounds of Formula Ia are those of Formula Ia-2:

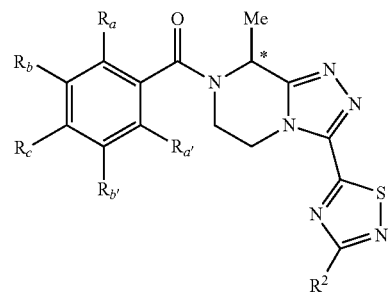

(Ia-2)

and pharmaceutically acceptable solvates thereof, wherein $R_a$, $R_{a'}$, $R_b$, $R_{b'}$, $R_c$ and $R^2$ are as defined in Formula I'.

In one embodiment, preferred compounds of Formula Ia-2 are those of Formula Ia-2':

(Ia-2')

and pharmaceutically acceptable solvates thereof, wherein $R_a$, $R_{a'}$, $R_b$, $R_{b'}$, $R_c$ and $R^2$ are as defined in Formula I'.

According to one embodiment, preferred compounds of Formula Ia-2 and Ia-2' and pharmaceutically acceptable solvates thereof are those wherein:

$R^2$ is methyl, ethyl, methoxymethyl, trifluoromethyl, difluoromethyl, fluoromethyl, 1-fluoroethyl, 1,1-difluoroethyl or 2,2,2-trifluoroethyl; more preferably $R^2$ is methyl, ethyl, methoxymethyl, trifluoromethyl, difluoromethyl or fluoromethyl; even more preferably $R^2$ is methyl;

$R_a$ is H;

$R_{a'}$ is H;

$R_b$ is H;

$R_{b'}$ is H; and $R_c$ is F.

In one embodiment, preferred compounds of Formula Ia are those of Formula Ia-3:

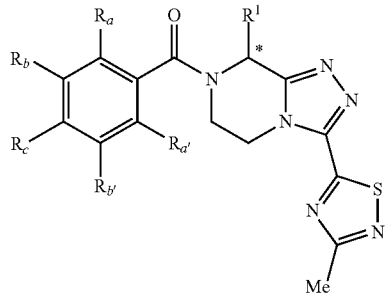

and pharmaceutically acceptable solvates thereof, wherein $R_a$, $R_{a'}$, $R_b$, $R_{b'}$, $R_c$ and $R^1$ are as defined in Formula I'.

In one embodiment, preferred compounds of Formula Ia-3 are those of Formula Ia-3':

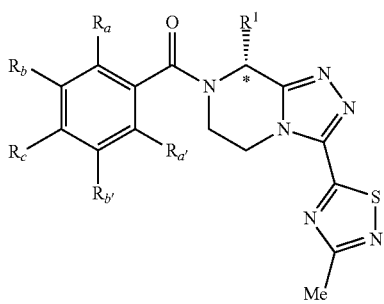

and pharmaceutically acceptable solvates thereof, wherein $R_a$, $R_{a'}$, $R_b$, $R_{b'}$, $R_c$ and $R^1$ are as defined in Formula I'.

In one embodiment, preferred compounds of Formula I are those of Formula Ib:

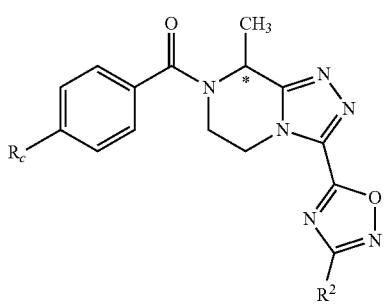

and pharmaceutically acceptable solvates thereof, wherein
  $R_c$ is F or thiophen-2-yl; preferably $R_c$ is F.
  $R^2$ is methyl, ethyl, methoxymethyl, trifluoromethyl, difluoromethyl, fluoromethyl, 1-fluoroethyl, 1,1-difluoroethyl or 2,2,2-trifluoroethyl, preferably $R^2$ is methyl, ethyl, trifluoromethyl, difluoromethyl or fluoromethyl, preferably $R^2$ is methyl, ethyl, 1-fluoroethyl, 1,1-difluoroethyl or 2,2,2-trifluoroethyl, preferably $R^2$ is methyl or ethyl, preferably $R^2$ is methyl.

According to one embodiment, compounds of Formula Ib do not comprise compound wherein $R_c$ is thiophen-2-yl when $R^2$ is methyl.

In one embodiment, preferred compounds of Formula Ib are those of Formula Ib':

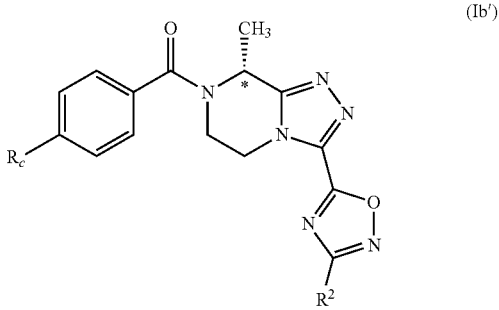

and pharmaceutically acceptable solvates thereof, wherein $R_c$ and $R^2$ are as defined in Formula Ib.

In one embodiment, preferred compounds of Formula Ib' are those wherein $R_c$ is F when $R^2$ is methyl.

In one embodiment, preferred compounds of Formula Ib' are those of Formula Ib-1:

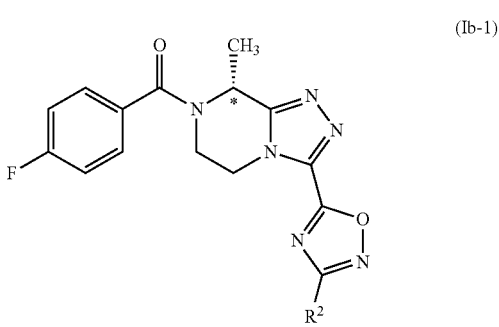

and pharmaceutically acceptable solvates thereof, wherein $R^2$ are as defined in Formula Ib.

In one embodiment, preferred compounds of Formula I are those of Formula Ic:

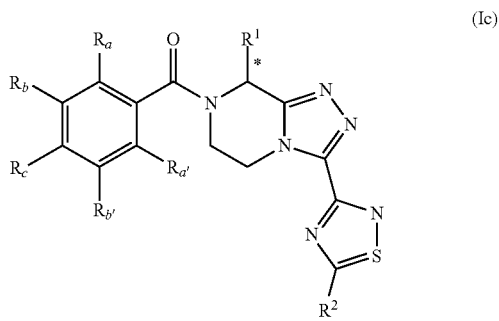

and pharmaceutically acceptable solvates thereof, wherein $R_a$, $R_{a'}$, $R_b$, $R_{b'}$, $R_c$, $R^1$ and $R^2$ are as defined in Formula I'.

In one embodiment, preferred compounds of Formula Ic are those of Formula Ic':

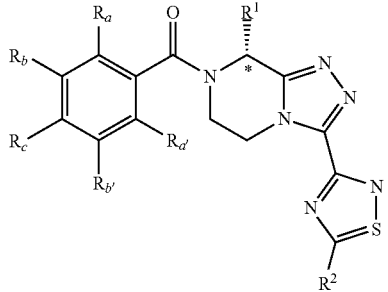

(Ic')

and pharmaceutically acceptable solvates thereof, wherein $R_a$, $R_{a'}$, $R_b$, $R_{b'}$, $R_c$, $R^1$ and $R^2$ are as defined in Formula Ic.

Preferred compounds of Formula Ic and Ic' and pharmaceutically acceptable solvates thereof are those wherein:

$R_a$ is H, F or methyl;

$R_{a'}$ is H;

$R_b$ is H, F, Cl or methoxy;

$R_{b'}$ is H or F;

$R_c$ is H, F, Cl, methyl, trifluoromethyl or nitrile;

$R^1$ is methyl, ethyl, n-propyl or hydroxyethyl;

$R^2$ is methyl, ethyl or trifluoromethyl.

Particularly preferred compounds of Formula I of the invention are those listed in Table 1 hereafter.

TABLE 1

| Cpd no | Structure | Chemical name | MW |
|---|---|---|---|
| 1 | 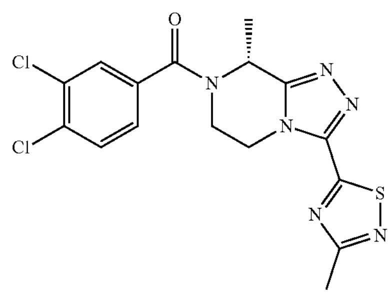 [SMILES: Cc1nsc(-c2nnc3n2CCN(C(=O)c2ccc(Cl)c(Cl)c2)[C@@H]3C)n1] | (R)-(3,4-dichlorophenyl)(8-methyl-3-(3-methyl-1,2,4-thiadiazol-5-yl)-5,6-dihydro-[1,2,4]triazolo[4,3-a]pyrazin-7(8H)-yl)methanone | 409.29 |
| 2 | 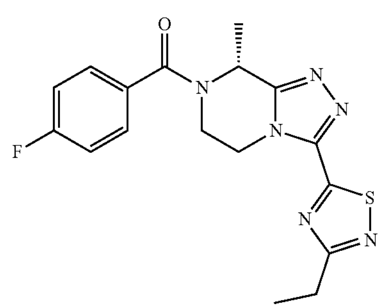 [SMILES: CCc1nsc(-c2nnc3n2CCN(C(=O)c2ccc(F)cc2)[C@@H]3C)n1] | (R)-(3-(3-ethyl-1,2,4-thiadiazol-5-yl)-8-methyl-5,6-dihydro-[1,2,4]triazolo[4,3-a]pyrazin-7(8H)-yl)(4-fluorophenyl)methanone | 372.42 |
| 3 | 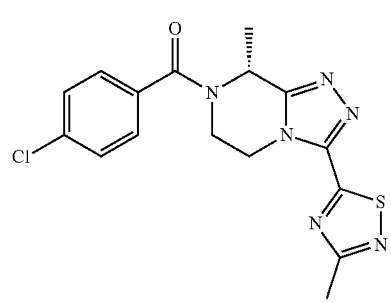 [SMILES: Cc1nsc(-c2nnc3n2CCN(C(=O)c2ccc(Cl)cc2)[C@@H]3C)n1] | (R)-(4-chlorophenyl)(8-methyl-3-(3-methyl-1,2,4-thiadiazol-5-yl)-5,6-dihydro-[1,2,4]triazolo[4,3-a]pyrazin-7(8H)-yl)methanone | 374.85 |

TABLE 1-continued

| Cpd no | Structure | Chemical name | MW |
|---|---|---|---|
| 4 | 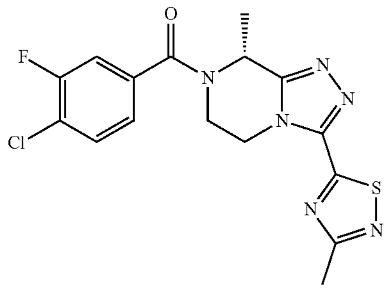 [SMILES: Cc1nsc(-c2nnc3n2CCN(C(=O)c2ccc(Cl)c(F)c2)[C@@H]3C)n1] | (R)-(4-chloro-3-fluorophenyl)(8-methyl-3-(3-methyl-1,2,4-thiadiazol-5-yl)-5,6-dihydro-[1,2,4]triazolo[4,3-a]pyrazin-7(8H)-yl)methanone | 392.84 |
| 5 | 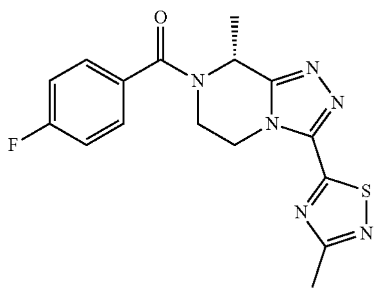 [SMILES: Cc1nsc(-c2nnc3n2CCN(C(=O)c2ccc(F)cc2)[C@@H]3C)n1] | (R)-(4-fluorophenyl)(8-methyl-3-(3-methyl-1,2,4-thiadiazol-5-yl)-5,6-dihydro-[1,2,4]triazolo[4,3-a]pyrazin-7(8H)-yl)methanone | 358.39 |
| 6 | 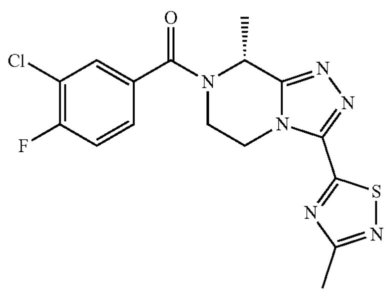 [SMILES: Cc1nsc(-c2nnc3n2CCN(C(=O)c2ccc(F)c(Cl)c2)[C@@H]3C)n1] | (R)-(3-chloro-4-fluorophenyl)(8-methyl-3-(3-methyl-1,2,4-thiadiazol-5-yl)-5,6-dihydro-[1,2,4]triazolo[4,3-a]pyrazin-7(8H)-yl)methanone | 392.84 |
| 7 | 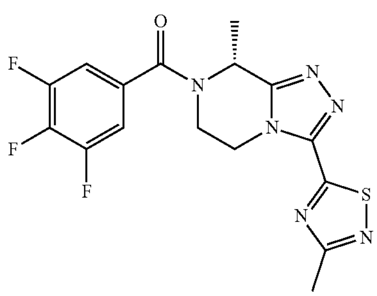 [SMILES: Cc1nsc(-c2nnc3n2CCN(C(=O)c2cc(F)c(F)c(F)c2)[C@@H]3C)n1] | (R)-(8-methyl-3-(3-methyl-1,2,4-thiadiazol-5-yl)-5,6-dihydro-[1,2,4]triazolo[4,3-a]pyrazin-7(8H)-yl)(3,4,5-trifluorophenyl)methanone | 394.37 |
| 8 | 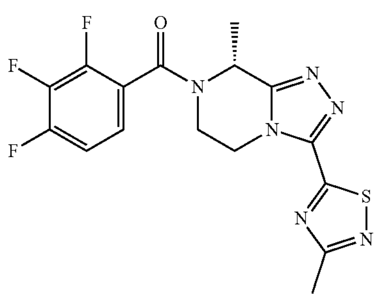 [SMILES: Cc1nsc(-c2nnc3n2CCN(C(=O)c2ccc(F)c(F)c2F)[C@@H]3C)n1] | (R)-(8-methyl-3-(3-methyl-1,2,4-thiadiazol-5-yl)-5,6-dihydro-[1,2,4]triazolo[4,3-a]pyrazin-7(8H)-yl)(2,3,4-trifluorophenyl)methanone | 394.37 |

TABLE 1-continued

| Cpd no | Structure | Chemical name | MW |
|---|---|---|---|
| 9 | 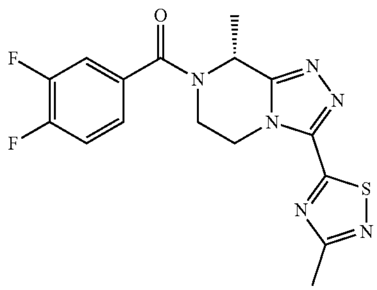 [SMILES: Cc1nsc(-c2nnc3n2CCN(C(=O)c2ccc(F)c(F)c2)[C@@H]3C)n1] | (R)-(3,4-difluorophenyl)(8-methyl-3-(3-methyl-1,2,4-thiadiazol-5-yl)-5,6-dihydro-[1,2,4]triazolo[4,3-a]pyrazin-7(8H)-yl)methanone | 376.38 |
| 10 | 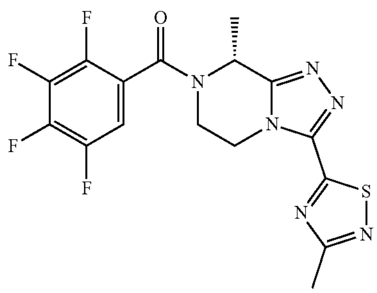 [SMILES: Cc1nsc(-c2nnc3n2CCN(C(=O)c2cc(F)c(F)c(F)c2F)[C@@H]3C)n1] | (R)-(8-methyl-3-(3-methyl-1,2,4-thiadiazol-5-yl)-5,6-dihydro-[1,2,4]triazolo[4,3-a]pyrazin-7(8H)-yl)(2,3,4,5-tetrafluorophenyl)methanone | 412.36 |
| 11 | 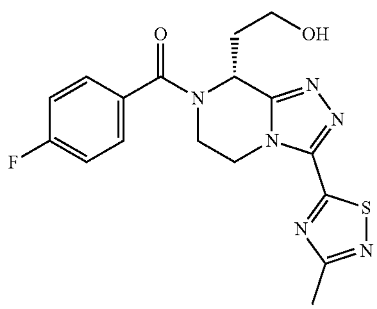 [SMILES: Cc1nsc(-c2nnc3n2CCN(C(=O)c2ccc(F)cc2)[C@@H]3CCO)n1] | (R)-(4-fluorophenyl)(8-(2-hydroxyethyl)-3-(3-methyl-1,2,4-thiadiazol-5-yl)-5,6-dihydro-[1,2,4]triazolo[4,3-a]pyrazin-7(8H)-yl)methanone | 388.42 |
| 12 | 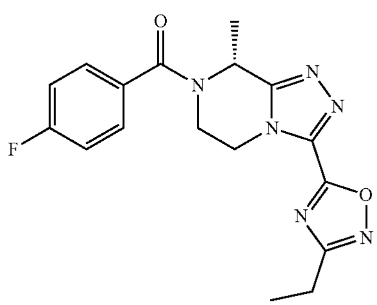 [SMILES: CCc1noc(-c2nnc3n2CCN(C(=O)c2ccc(F)cc2)[C@@H]3C)n1] | (R)-(3-(3-ethyl-1,2,4-oxadiazol-5-yl)-8-methyl-5,6-dihydro-[1,2,4]triazolo[4,3-a]pyrazin-7(8H)-yl)(4-fluorophenyl)methanone | 356.35 |
| 13 | 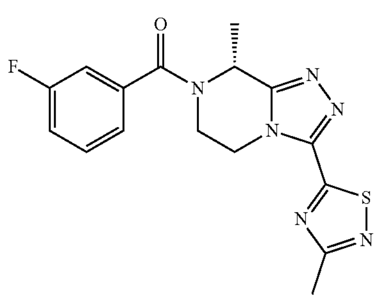 [SMILES: Cc1nsc(-c2nnc3n2CCN(C(=O)c2cccc(F)c2)[C@@H]3C)n1] | (R)-(3-fluorophenyl)(8-methyl-3-(3-methyl-1,2,4-thiadiazol-5-yl)-5,6-dihydro-[1,2,4]triazolo[4,3-a]pyrazin-7(8H)-yl)methanone | 358.39 |

TABLE 1-continued

| Cpd no | Structure | Chemical name | MW |
|---|---|---|---|
| 14 | 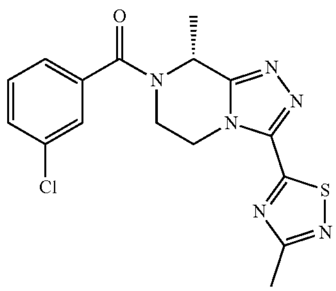 [SMILES: Cc1nsc(-c2nnc3n2CCN(C(=O)c2cccc(Cl)c2)[C@@H]3C)n1] | (R)-(3-chlorophenyl)(8-methyl-3-(3-methyl-1,2,4-thiadiazol-5-yl)-5,6-dihydro-[1,2,4]triazolo[4,3-a]pyrazin-7(8H)-yl)methanone | 374.85 |
| 15 | 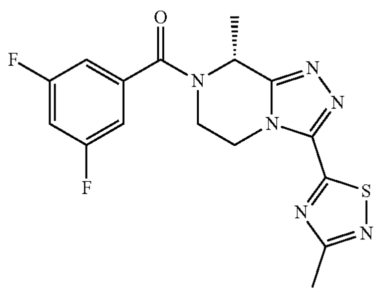 [SMILES: Cc1nsc(-c2nnc3n2CCN(C(=O)c2cc(F)cc(F)c2)[C@@H]3C)n1] | (R)-(3,5-difluorophenyl)(8-methyl-3-(3-methyl-1,2,4-thiadiazol-5-yl)-5,6-dihydro-[1,2,4]triazolo[4,3-a]pyrazin-7(8H)-yl)methanone | 376.38 |
| 16 | 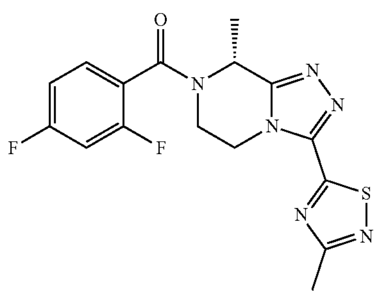 [SMILES: Cc1nsc(-c2nnc3n2CCN(C(=O)c2ccc(F)cc2F)[C@@H]3C)n1] | (R)-(2,4-difluorophenyl)(8-methyl-3-(3-methyl-1,2,4-thiadiazol-5-yl)-5,6-dihydro-[1,2,4]triazolo[4,3-a]pyrazin-7(8H)-yl)methanone | 376.38 |
| 17 | 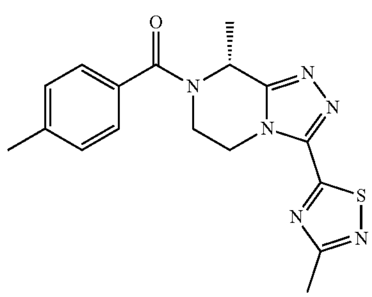 [SMILES: Cc1ccc(C(=O)N2CCn3c(-c4nc(C)ns4)nnc3[C@H]2C)cc1] | (R)-(8-methyl-3-(3-methyl-1,2,4-thiadiazol-5-yl)-5,6-dihydro-[1,2,4]triazolo[4,3-a]pyrazin-7(8H)-yl)(p-tolyl)methanone | 354.43 |
| 18 | 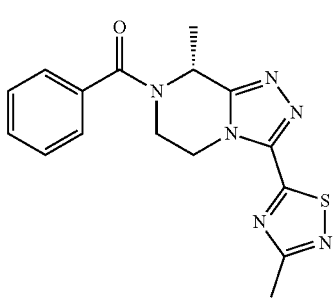 [SMILES: Cc1nsc(-c2nnc3n2CCN(C(=O)c2ccccc2)[C@@H]3C)n1] | (R)-(8-methyl-3-(3-methyl-1,2,4-thiadiazol-5-yl)-5,6-dihydro-[1,2,4]triazolo[4,3-a]pyrazin-7(8H)-yl)(phenyl)methanone | 340.4 |

TABLE 1-continued

| Cpd no | Structure | Chemical name | MW |
|---|---|---|---|
| 19 | 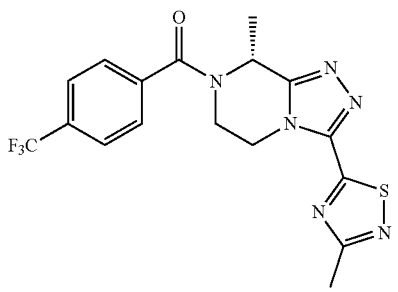 [SMILES: Cc1nsc(-c2nnc3n2CCN(C(=O)c2ccc(C(F)(F)F)cc2)[C@@H]3C)n1] | (R)-(8-methyl-3-(3-methyl-1,2,4-thiadiazol-5-yl)-5,6-dihydro-[1,2,4]triazolo[4,3-a]pyrazin-7(8H)-yl)(4-(trifluoromethyl)phenyl)methanone | 408.4 |
| 20 | 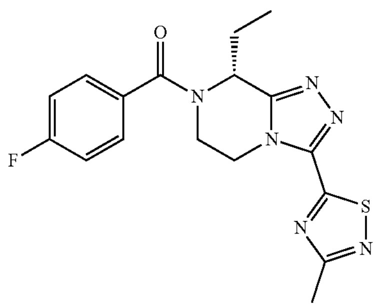 [SMILES: CC[C@@H]1c2nnc(-c3nc(C)ns3)n2CCN1C(=O)c1ccc(F)cc1] | (R)-(8-ethyl-3-(3-methyl-1,2,4-thiadiazol-5-yl)-5,6-dihydro-[1,2,4]triazolo[4,3-a]pyrazin-7(8H)-yl)(4-fluorophenyl)methanone | 372.42 |
| 21 | 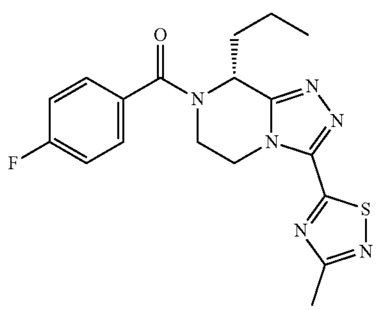 [SMILES: CCC[C@@H]1c2nnc(-c3nc(C)ns3)n2CCN1C(=O)c1ccc(F)cc1] | (R)-(4-fluorophenyl)(3-(3-methyl-1,2,4-thiadiazol-5-yl)-8-propyl-5,6-dihydro-[1,2,4]triazolo[4,3-a]pyrazin-7(8H)-yl)methanone | 386.45 |
| 22 | 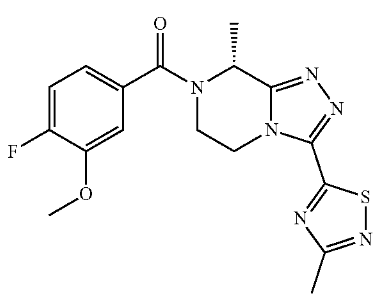 [SMILES: COc1cc(C(=O)N2CCn3c(-c4nc(C)ns4)nnc3[C@H]2C)ccc1F] | (R)-(4-fluoro-3-methoxyphenyl)(8-methyl-3-(3-methyl-1,2,4-thiadiazol-5-yl)-5,6-dihydro-[1,2,4]triazolo[4,3-a]pyrazin-7(8H)-yl)methanone | 388.42 |
| 23 | 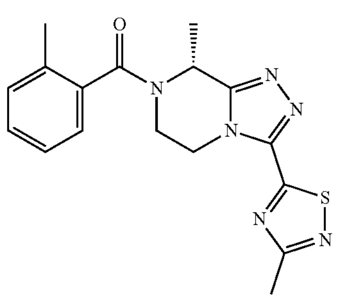 [SMILES: Cc1nsc(-c2nnc3n2CCN(C(=O)c2ccccc2C)[C@@H]3C)n1] | (R)-(8-methyl-3-(3-methyl-1,2,4-thiadiazol-5-yl)-5,6-dihydro-[1,2,4]triazolo[4,3-a]pyrazin-7(8H)-yl)(o-tolyl)methanone | 354.43 |

TABLE 1-continued

| Cpd no | Structure | Chemical name | MW |
|---|---|---|---|
| 24 | 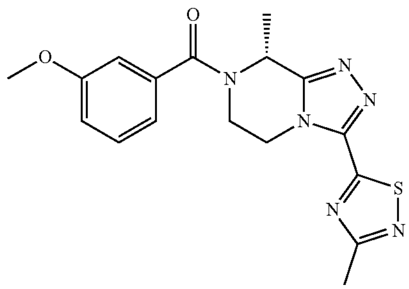 [SMILES: COc1cccc(C(=O)N2CCn3c(-c4nc(C)ns4)nnc3[C@H]2C)c1] | (R)-(3-methoxyphenyl)(8-methyl-3-(3-methyl-1,2,4-thiadiazol-5-yl)-5,6-dihydro-[1,2,4]triazolo[4,3-a]pyrazin-7(8H)-yl)methanone | 370.43 |
| 25 | 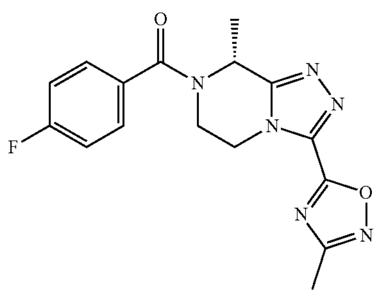 [SMILES: Cc1noc(-c2nnc3n2CCN(C(=O)c2ccc(F)cc2)[C@@H]3C)n1] | (R)-(4-fluorophenyl)(8-methyl-3-(3-methyl-1,2,4-oxadiazol-5-yl)-5,6-dihydro-[1,2,4]triazolo[4,3-a]pyrazin-7(8H)-yl)methanone | 342.33 |
| 26 | 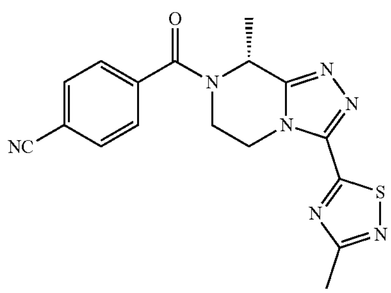 [SMILES: Cc1nsc(-c2nnc3n2CCN(C(=O)c2ccc(C#N)cc2)[C@@H]3C)n1] | (R)-4-(8-methyl-3-(3-methyl-1,2,4-thiadiazol-5-yl)-5,6,7,8-tetrahydro-[1,2,4]triazolo[4,3-a]pyrazine-7-carbonyl)benzonitrile | 365.41 |
| 27 | 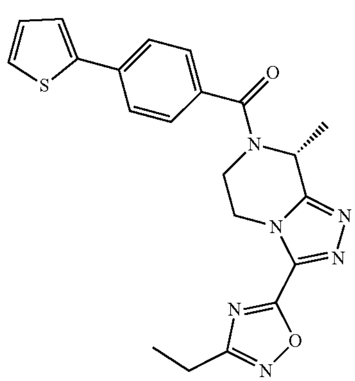 [SMILES: CCc1noc(-c2nnc3n2CCN(C(=O)c2ccc(-c4cccs4)cc2)[C@@H]3C)n1] | (R)-(3-(3-ethyl-1,2,4-oxadiazol-5-yl)-8-methyl-5,6-dihydro-[1,2,4]triazolo[4,3-a]pyrazin-7(8H)-yl)(4-(thiophen-2-yl)phenyl)methanone | 420.49 |
| 28 | 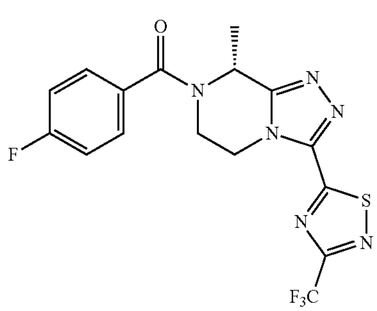 [SMILES: C[C@@H]1c2nnc(-c3nc(C(F)(F)F)ns3)n2CCN1C(=O)c1ccc(F)cc1] | (R)-(4-fluorophenyl)(8-methyl-3-(3-(trifluoromethyl)-1,2,4-thiadiazol-5-yl)-5,6-dihydro-[1,2,4]triazolo[4,3-a]pyrazin-7(8H)-yl)methanone | 412.36 |

TABLE 1-continued

| Cpd no | Structure | Chemical name | MW |
|---|---|---|---|
| 29 | 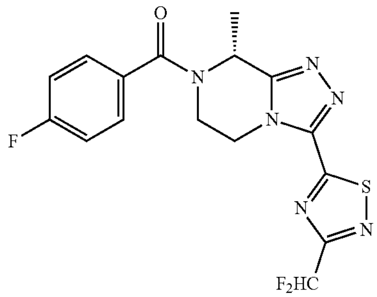 [SMILES: C[C@@H]1c2nnc(-c3nc(C(F)F)ns3)n2CCN1C(=O)c1ccc(F)cc1] | (R)-(3-(3-(difluoromethyl)-1,2,4-thiadiazol-5-yl)-8-methyl-5,6-dihydro-[1,2,4]triazolo[4,3-a]pyrazin-7(8H)-yl)(4-fluorophenyl)methanone | 394.37 |
| 30 | 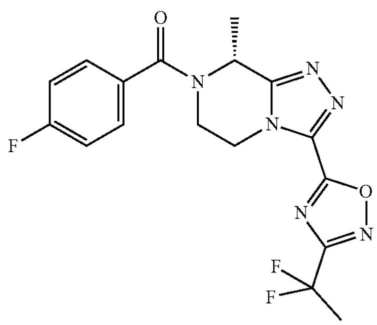 [SMILES: C[C@@H]1c2nnc(-c3nc(C(C)(F)F)no3)n2CCN1C(=O)c1ccc(F)cc1] | (R)-(3-(3-(1,1-difluoroethyl)-1,2,4-oxadiazol-5-yl)-8-methyl-5,6-dihydro-[1,2,4]triazolo[4,3-a]pyrazin-7(8H)-yl)(4-fluorophenyl)methanone | 392.34 |
| 31 | 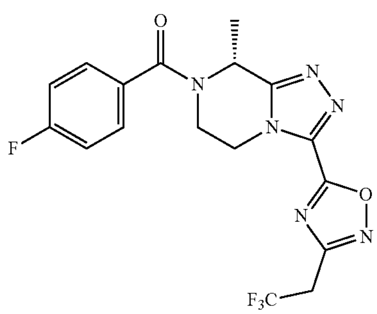 [SMILES: C[C@@H]1c2nnc(-c3nc(CC(F)(F)F)no3)n2CCN1C(=O)c1ccc(F)cc1] | (R)-(4-fluorophenyl)(8-methyl-3-(3-(2,2,2-trifluoroethyl)-1,2,4-oxadiazol-5-yl)-5,6-dihydro-[1,2,4]triazolo[4,3-a]pyrazin-7(8H)-yl)methanone | 410.33 |
| 32 | 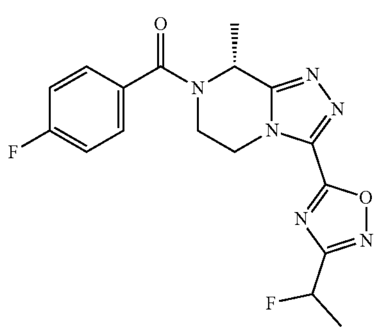 [SMILES: CC(F)c1noc(-c2nnc3n2CCN(C(=O)c2ccc(F)cc2)[C@@H]3C)n1] | ((8R)-3-(3-(1-fluoroethyl)-1,2,4-oxadiazol-5-yl)-8-methyl-5,6-dihydro-[1,2,4]triazolo[4,3-a]pyrazin-7(8H)-yl)(4-fluorophenyl)methanone | 374.34 |

In Table 1, the term "Cpd" means compound.

The compounds of Table 1 were named using ChemBioDraw® Ultra version 12.0 (PerkinElmer).

Synthesis Intermediates

In another aspect, the invention provides intermediates for the synthesis of compounds of Formula I, in particular according to the process of the invention.

Especially, the process of the invention provides compounds of general Formula C:

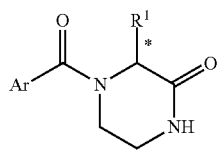

(C)

and pharmaceutically acceptable solvates thereof, wherein Ar and $R^1$ are as defined in Formula I.

In one embodiment, preferred compounds of Formula C or solvates thereof are those of Formula C-a:

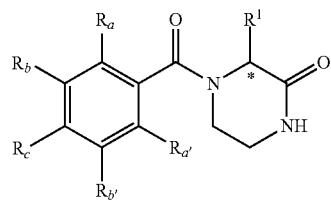

(C-a)

and pharmaceutically acceptable solvates thereof, wherein $R^1$ is alkyl, haloalkyl, hydroxyalkyl or alkoxyalkyl, preferably $R^1$ is methyl, ethyl, n-propyl, hydroxyethyl, methoxyethyl, trifluoromethyl, difluoromethyl or fluoromethyl; more preferably $R^1$ is methyl;

$R_a$, $R_{a'}$, $R_b$, $R_{b'}$ and $R_c$ represent independently H, halo, alkyl, alkoxy, haloalkyl, nitrile or thiophen-2-yl; preferably H, F, Cl, methyl, methoxy, trifluoromethyl, nitrile or thiophen-2-yl; more preferably H or F.

In one preferred embodiment, compound of Formula C is the (R)-enantiomer.

In one embodiment, preferred compounds of Formula C or solvates thereof are those of Formula C-b:

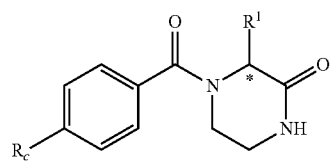

(C-b)

and pharmaceutically acceptable solvates thereof, wherein, $R_c$ and $R^1$ are as defined in Formula C-a.

In one embodiment, preferred compounds of Formula C and solvates thereof are those of Formula C-b':

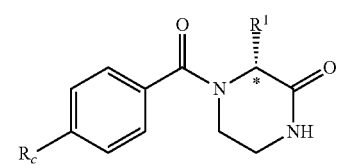

(C-b')

and pharmaceutically acceptable solvates thereof, wherein $R_c$ and $R^1$ are as defined in Formula C-a.

In one embodiment, preferred compounds of Formula C and solvates thereof are those of Formula C-a-1:

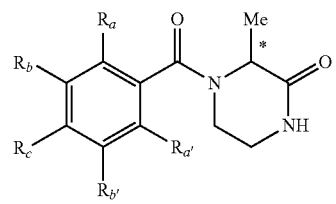

(C-a-1)

and pharmaceutically acceptable solvates thereof, wherein $R_a$, $R_{a'}$, $R_b$, $R_{b'}$ and $R_c$ are as defined in Formula C-a.

In one embodiment, preferred compounds of Formula C and solvates thereof are those of Formula C-a-1':

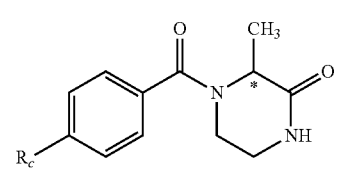

(C-a-1)

and pharmaceutically acceptable solvates thereof, wherein $R_a$, $R_{a'}$, $R_b$, $R_{b'}$ and $R_c$ are as defined in Formula C-a.

In one embodiment, preferred compounds of Formula C and solvates thereof are those of Formula C-b1:

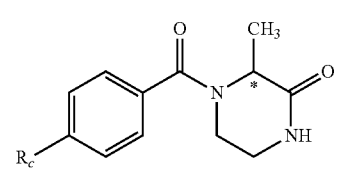

(C-b1)

and pharmaceutically acceptable solvates thereof, wherein $R_c$ is as defined in Formula C-a.

In one embodiment, preferred compounds of Formula C and solvates thereof are those of Formula C-b1':

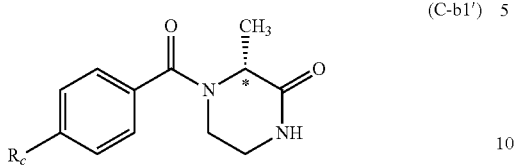
(C-b1')

and pharmaceutically acceptable solvates thereof, wherein $R_c$ is as defined in Formula C-a.

In one preferred embodiment, preferred compounds of Formula C and solvates thereof are compound of Formula C-b2:

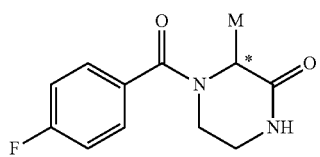
(C-b2)

In one embodiment, preferred compounds of Formula C and solvates thereof are compound of Formula C-b2':

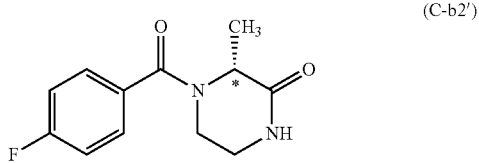 [SMILES: C[C@@H]1C(=O)NCCN1C(=O)c1ccc(F)cc1]
(C-b2')

and pharmaceutically acceptable solvates thereof.

The process of the invention also provides compounds of general Formula D:

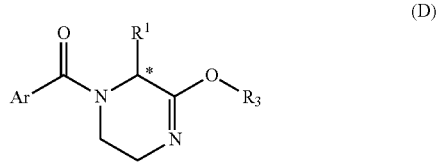
(D)

and pharmaceutically acceptable solvates thereof, wherein Ar and $R^1$ are as defined above, and $R^3$ is C1-C2 alkyl.

In a preferred embodiment, compound of Formula D is compound of Formula D-1 ((3-ethoxy-2-methyl-5,6-dihydropyrazin-1(2H)-yl)(4-fluorophenyl)methanone):

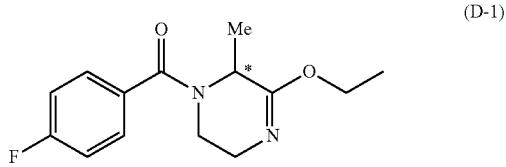 [SMILES: CCOC1=NCCN(C(=O)c2ccc(F)cc2)C1C]
(D-1)

In one preferred embodiment, compound of Formula D is the (R)-enantiomer.

Definitions

In the present invention, the following terms have the following meanings:

The term "about" preceding a figure means plus or less 10% of the value of said figure.

The term "halo" or "halogen" means fluoro, chloro, bromo, or iodo. Preferred halo groups are fluoro and chloro.

The term "alkyl" by itself or as part of another substituent refers to a hydrocarbyl radical of Formula $C_nH_{2n+1}$ wherein n is a number greater than or equal to 1. "Cx-Cy-alkyl" refer to alkyl groups which comprise from x to y carbon atoms. Generally, alkyl groups of this invention comprise from 1 to 4 carbon atoms (C1-C4), preferably from 1 to 3 carbon atoms (C1-C3), more preferably from 1 to 2 carbon atoms (C1-C2). Alkyl groups may be linear or branched. Suitable alkyl groups include but are not limited to methyl, ethyl, n-propyl, i-propyl, n-butyl, i-butyl, s-butyl and t-butyl.

The term "haloalkyl" alone or in combination, refers to an alkyl radical having the meaning as defined above wherein one or more hydrogens are replaced with a halogen as defined above. Non-limiting examples of such haloalkyl radicals include chloromethyl, 1-bromoethyl, fluoromethyl, difluoromethyl, trifluoromethyl, 1,1,1-trifluoroethyl and the like.

The term "alkoxy" refers to any group —O-alkyl, wherein alkyl is as defined above. Suitable alkoxy groups include for example methoxy, ethoxy, n-propoxy, isopropoxy, n-butoxy, f-butoxy, sec-butoxy, and n-pentoxy.

The term "alkoxyalkyl" refers to any group -alkyl-O-alkyl, wherein alkyl is as defined above.

The term "hydroxyalkyl" refers to any group -alkyl-OH, wherein alkyl is as defined above. The term "(C1-C2) hydroxyalkyl" refers to any (C1-C2)alkyl-OH.

The term "(C1-C2)alkylsulfate" refers to any (C1-C2) alkyl-O—$SO_3^-$ compound, wherein alkyl is as defined above.

The term "(C1-C2)chloroformate" refers to any (C1-C2) alkyl-O—COCl compound, wherein alkyl is as defined above.

The term "tri(C1-C2 alkyl)oxonium salt" refers to any salt of [C1-C2)alkyl]$_3$-O$^+$, wherein alkyl is as defined above.

The term "thiophen-2-yl" as used herein means a group of formula

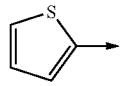

wherein the arrow defines the attachment point.

The term "ester" or "esters" as used herein means a group selected the group consisting of unsubstituted C1-C4 alkyloxycarbonyl, unsubstituted phenyloxycarbonyl or unsubstituted phenyl(C1-C2 alkyl)oxycarbonyl. Suitable ester groups include methyloxycarbonyl, ethyloxycarbonyl, n-propyloxycarbonyl, i-propyloxycarbonyl, n-butyloxycarbonyl, i-butyloxycarbonyl, s-butyloxycarbonyl, t-butyloxycarbonyl, phenyloxycarbonyl, benzyloxycarbonyl and phenethyloxycarbonyl, among which methyloxycarbonyl, ethyloxycarbonyl, propyloxycarbonyl, i-propyloxycarbonyl, phenyloxycarbonyl, and benzyloxycarbonyl are preferred.

The term "protecting group" refers to a suitable organic moiety used to protect a certain functional group in a chemical synthesis. In the present invention, protecting group refers to an organic moiety selected from 2,4-dimethoxybenzyl (DMB), 4-methoxybenzyl (PMB), tert-butoxycarbonyl (Boc), allyl, diphenyl-phosphiramide (DPP) and/or 2-trimethylsilylethanesulfonyl (SES).

The numbering scheme for N-acyl-(3-substituted)-(8-substituted)-5,6-dihydro-[1,2,4]triazolo[4,3-a]pyrazines of the invention is shown in the below:

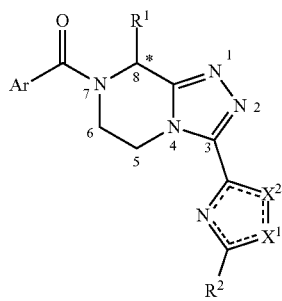

The compounds of Formula I and subformulae thereof contain a stereogenic carbon center at position 8 and thus may exist as (R)- and (S)-enantiomers. The use of a solid line to depict the bond between position 8 of the ring and $R^1$, with a star next to position 8, (i.e. ——) indicates that the individual enantiomers are meant, thus excluding racemic mixtures thereof.

A solid wedge (▬) for the bond between position 8 of the ring and $R^1$ is used to depict the (S)-enantiomer and a dotted wedge (·····) for the bond between position 8 of the ring and $R^1$ is used to depict the (R)-enantiomer.

The term "solvate" is used herein to describe a compound in this invention that contain stoechiometric or sub-stoechiometric amounts of one or more pharmaceutically acceptable solvent molecule such as ethanol. The term "hydrate" refers to when the said solvent is water.

All references to compounds of Formula I include references to solvates, multi-component complexes and liquid crystals thereof.

The compounds of the invention include compounds of Formula I, Formula C and Formula D as hereinbefore defined, including all polymorphs and crystal habits thereof, prodrugs and isomers thereof (including tautomeric isomers) and isotopically-labeled compounds of Formula I.

In addition, with respect to the salts of the compounds of the invention, it should be noted that the invention in its broadest sense also included salts, which may for example be used in the isolation and/or purification of the compounds of the invention. For example, salts formed with optically active acids or bases may be used to form diastereoisomeric salts that can facilitate the separation of optically active isomers of the compounds of Formula E above.

Examples

The present invention will be better understood with reference to the following examples. These examples are intended to be representative of specific embodiments of the invention, and are not intended as limiting the scope of the invention.

Chemistry Examples

Reaction schemes as described in the example section illustrate by way of example different possible approaches.

All reported temperatures are expressed in degrees Celsius (° C.); all reactions were carried out at room temperature (RT) unless otherwise stated.

All reactions were followed by thin layer chromatography (TLC) analysis (TLC plates, silica gel 60 $F_{254}$, Merck) was used to monitor reactions, establish silica-gel flash chromatography conditions. All other TLC developing agents/visualization techniques, experimental set-up or purification procedures that were used in this invention, when not described in specific details, are assumed to be known to those conversant in the art and are described in such standard reference manuals as: i) Gordon, A. J.; Ford, R. A. "The Chemist's Companion—A Handbook of Practical Data, Techniques, and References", Wiley: New York, 1972; ii) Vogel's Textbook of Practical Organic Chemistry, Pearson Prentice Hall: London, 1989.

HPLC-MS spectra were typically obtained on an Agilent LCMS using electropsray ionization (ESI). The Agilent instrument includes an autosampler 1200, a binary pump 1100, an ultraviolet multi-wavelength detector 1100 and a 6100 single-quad mass-spectrometer. The chromatography column used was Sunfire 3.5 μm, C18, 3.0×50 mm in dimensions. Eluent typically used was a mixture of solution A (0.1% TFA in $H_2O$) and solution B (0.1% TFA in MeCN). Gradient was applied at a flow rate of 1.3 mL per minute as follows: gradient A: held the initial conditions of 5% solution B for 0.2 min, increased linearly to 95% solution B in 6 min, held at 95% during 1.75 min, returned to initial conditions in 0.25 min and maintained for 2.0 min; gradient B: held the initial conditions of 5% solution B for 0.2 min, increased linearly to 95% in 2.0 min, held at 95% during 1.75 min, returned to initial conditions in 0.25 min and maintained for 2 min.

Determination of chiral purity was made using chiral HPLC that was performed on an Agilent 1100 (binary pump and a ultraviolet multi wavelength detector) with manual or automatic (Autosampler 1100) injection capabilities. Column used is CHIRALPAK IA 5 μm, 4.6×250 mm in isocratic mode. Choice of eluent was predicated on the specifics of each separation. Further details concerning the chiral HPLC methods used are provided below:

Method A: column CHIRALPAK IA 5 μm, 4.6×250 mm, eluent: DCM/EtOH (98:2 v/v) plus 0.1% of DEA, flow rate: 1.0 mL per minute; UV detection at 254 nm; column at RT, eluent was used as sample solvent.

Method B: column CHIRALPAK IA 5 μm 4.6×250 mm, eluent: MTBE plus 0.1% of DEA, flow rate: 1.0 mL per minute; UV detection at 254 nm, column at RT, eluent was used as sample solvent.

$^1H$ (300 MHz), $^{19}F$-NMR (282 MHz) and $^{13}C$ NMR (75 MHz) spectra were recorded on a Bruker Avance ARX 300 instrument. Chemical shifts are expressed in parts per million, (ppm, δ units). Coupling constants are expressed in Hertz (Hz). Abbreviations for multiplicities observed in NMR spectra are as follows: s (singlet), d (doublet), t (triplet), q (quadruplet), m (multiplet), br (broad).

Solvents, reagents and starting materials were purchased and used as received from commercial vendors unless otherwise specified.

The following abbreviations are used:
DCM: Dichloromethane,
DEA: diethylamine,
ee: Enantiomeric excess,
EtOAc: Ethyl acetate,
EtOH: Ethanol,
L: Liter(s),
MeOH: Methanol, mL: Milliliter(s), mmol: Millimole(s), min: Minute(s), MTBE: methyl tert-butyl ether, P: UV purity at 254 nm or 215 nm determined by HPLC-MS, RT: Room temperature.

All compounds disclosed in the present application were named using ChemDraw Ultra 12® purchased from CambridgeSoft (Cambridge, Mass., USA).

Scheme 1: General synthetic scheme.

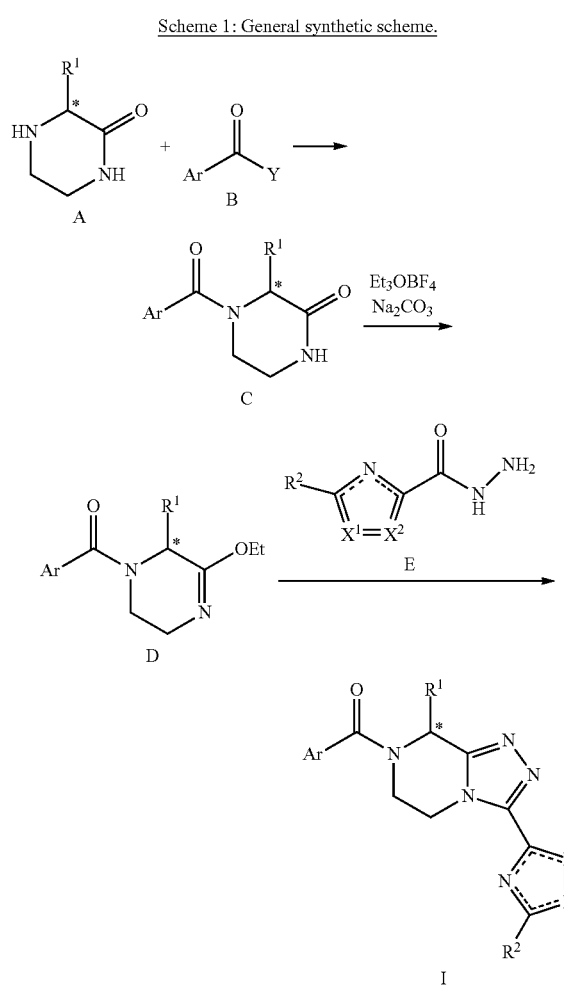

General Method A: Acylation of Ketopiperazine A by B to Afford C

Scheme 2: Acylation of A.

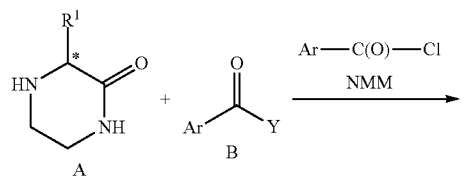

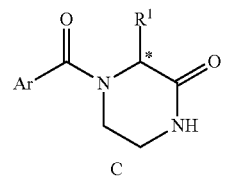

General Method A is illustrated by the synthesis of intermediate (R)-4-(4-fluorobenzoyl)-3-methylpiperazin-2-one (i.e. compound C wherein Ar is 4-F-Ph and $R^1$ is (R)-Me).

To a solution of (R)-3-methylpiperazin-2-one (14 g, 123 mmol) in commercial anhydrous DCM (400 mL) at RT was added 4-methylmorpholine (12.8 mL, 125 mmol) dropwise over 1 min, followed by 4-fluorobenzoyl chloride (14.5 mL, 123 mmol) dropwise over 5 min. The reaction mixture was stirred at RT for 10 min and then washed with HCl (1M, 150 mL) and NaOH (1M, 150 mL). The organic layer was dried over $MgSO_4$, filtered and evaporated under reduced pressure (1-2 mbar). The residue obtained was solubilized in a hot mixture of DCM (140 mL) and MTBE (315 mL). Pentane (350 mL) was then added until a cloudy solution was obtained. After 5 min at RT and 14 h at 4° C. (freezer), the white crystals were filtered off, washed with pentane (140 mL) and dried under vacuum (1-2 mbar, 40° C.) for 1 hour to afford white needles. Yield: 27.6 g, 95%. HPLC-MS: P >99%, $t_R$=1.8 min, (M+H)$^+$: 237; Chiral HPLC—Method A: % ee >99.9; $^1$H-NMR (CDCl$_3$): δ 7.4 (m, 2H), 7.1 (m, 2H), 6.4 (bs, 1H), 4.8 (m, 1H), 4.3 (m, 1H), 3.5 (m, 1H), 3.3 (m, 2H), 1.5 (d, J=6.9 Hz, 3H); $^{19}$F-NMR (CDCl$_3$): δ −97.4 (s, 1F).

General Method B: Iminoether D Formation from Acylated Ketopiperazine C

Scheme 3: Iminoether formation.

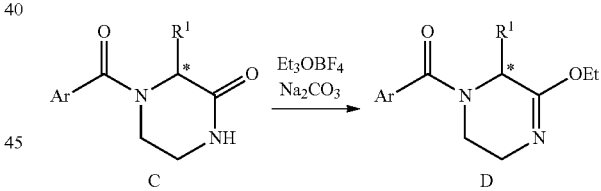

General Method B is illustrated by the synthesis of intermediate (R)-(3-ethoxy-2-methyl-5,6-dihydropyrazin-1(2H)-yl)(4-fluorophenyl)methanone (i.e. compound D wherein Ar is 4-F-Ph and $R^1$ is (R)-Me).

To a suspension of sodium carbonate (0.3 g, 2.86 mmol) in DCM (1.3 mL) at 0° C. was added (R)-4-(4-fluorobenzoyl)-3-methylpiperazin-2-one (0.3 g, 1.27 mmol) in one portion, followed by commercial triethyloxonium tetrafluoroborate (0.3 g, 1.59 mmol) in one portion. Thereafter the reaction mixture was stirred further at RT for 45 min, whereupon the reaction mixture was diluted with brine (20 mL). The layers were separated and the aqueous layer was further extracted with DCM (20 mL). The organic layers were combined, dried over $MgSO_4$, filtered and concentrated under reduced pressure. The crude compound was then purified on silica gel (EtOAc) to afford the desired product as colorless oil. Yield: 0.16 g, 47%. HPLC-MS: P=96%, $t_R$=1.8 min, (M+H$_2$O+H)$^+$: 283; Chiral HPLC—Method B: % ee >99.9; $^1$H-NMR (CDCl$_3$): δ 7.4 (m, 2H), 7.1 (m, 2H), 4.9 (m, 1H), 4.1 (m, 2H), 3.5 (m, 3H), 3.1 (m, 1H), 1.4 (m, 3H), 1.2 (m, 3H); $^{19}$F-NMR (CDCl$_3$): δ −96.7 (s, 1F).

General Method C: Triazolopiperazine I Formation from Iminoether D

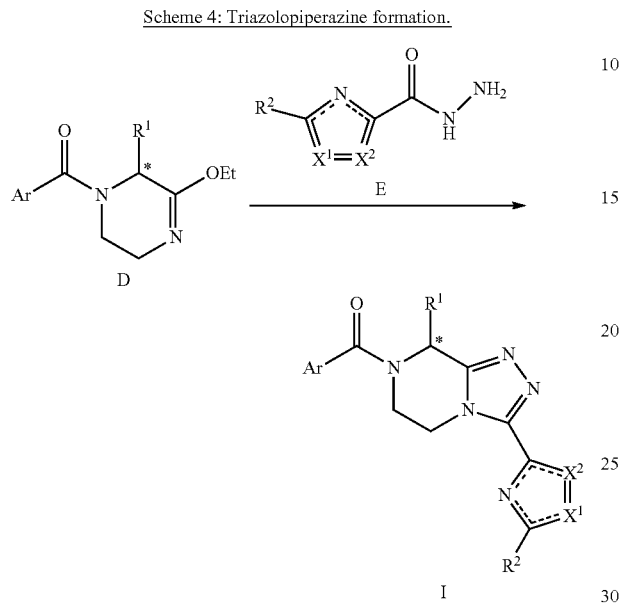

General Method C is illustrated by the synthesis of (R)-(4-fluorophenyl)(8-methyl-3-(3-methyl-1,2,4-thiadiazol-5-yl)-5,6-dihydro-[1,2,4]triazolo[4,3-a]pyrazin-7(8H)-yl)methanone (i.e. compound I wherein Ar is 4-F-Ph, R$^1$ is (R)-Me, R$^2$ is Me, X$^1$=N and X$^2$=S—Compound 1).

To (R)-(3-ethoxy-2-methyl-5,6-dihydropyrazin-1(2H)-yl) (4-fluorophenyl) (0.16 g, 0.6 mmol) at RT was added 3-methyl-1,2,4-thiadiazole-5-carbohydrazide (0.10 g, 0.6 mmol) in one portion. The mixture was diluted with commercially anhydrous MeOH (0.6 mL) and the resulting mixture was heated to 70° C. for 5 h.

The reaction mixture was then allowed to reach RT whereupon the solvent was removed under reduced pressure (1-2 mbar). The crude residue was then dissolved in DCM (25 mL), and thus-obtained organic phase washed with NaOH (1 M, 25 mL) and HCl (1 M, 25 mL). The organic layer was then dried over MgSO$_4$, filtered and concentrated under reduced pressure (1-2 mbar) to afford the desired product as colorless oil. Yield: 0.10 g, 45%.

Compound 1: HPLC-MS: P=94%, t$_R$=2.1 min, (M+H)$^+$: 359; chiral HPLC: % ee=96.7; $^1$H-NMR (CDCl$_3$): δ 7.5 (m, 2H), 7.3 (m, 2H), 5.8 (m, 1H), 4.9 (m, 1H), 4.6 (m, 1H), 4.3 (m, 1H), 3.5 (m, 1H), 2.7 (s, 3H), 1.7 (d, J=6.9 Hz, 3H); $^{19}$F-NMR (CDCl$_3$): δ −98.4 (s, 1F).

The following compound was also prepared from the ad hoc reagents using General Method C:

Compound 2: From 3-methyl-1,2,4-oxadiazole-5-carbohydrazide (48 h at 60° C., crude compound purified on silica gel (EtOAc/MeOH 99/1)). Yield: 0.14 g, 53%. HPLC-MS: P >98%, t$_R$=2.0 min, (M+H)$^+$: 343; chiral HPLC: % ee=92.0; $^1$H-NMR (CDCl$_3$): δ 7.5 (m, 2H), 7.2 (m, 2H), 5.8 (m, 1H), 4.9 (dd, J=3.3, 13.5 Hz, 1H), 4.6 (m, 1H), 4.3 (td, J=4.0, 12.8 Hz, 1H), 3.5 (m, 1H), 2.5 (s, 3H), 1.7 (d, J=6.9 Hz, 3H); $^{19}$F-NMR (CDCl$_3$): δ −98.3 (s, 1F).

The invention claimed is:

1. A process of preparing a chiral N-acyl-(3-substituted)-(8-substituted)-5,6-dihydro-[1,2,4]triazolo[4,3-a]pyrazine of general Formula I:

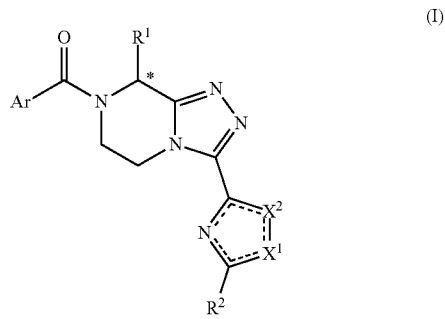

or a solvate thereof, wherein

R$^1$ is alkyl, haloalkyl, hydroxyalkyl or alkoxyalkyl;

R$^2$ is alkyl, alkoxyalkyl or haloalkyl;

Ar is an unsubstituted phenyl group or a phenyl group substituted by one or more substituent(s) selected from the group consisting of halo, alkyl, alkoxy, haloalkyl, nitrile, and thiophen-2-yl;

X$^1$ is N and X$^2$ is S or O; or X$^1$ is S and X$^2$ is N;

=== represents a single or a double bound depending on X$^1$ and X$^2$; and

* and the solid line extending from R$^1$ signify individual enantiomers, excluding racemic mixtures thereof;

said process comprising the following steps:

a) reacting a compound of Formula A:

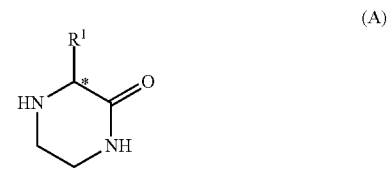

wherein R$^1$ is as defined above and

* and the solid line extending from R$^1$ signify individual enantiomers, excluding racemic mixtures thereof;

with a compound of Formula B:

wherein Ar is as defined above; and Y is hydroxyl or halo;
to obtain a compound of Formula C:

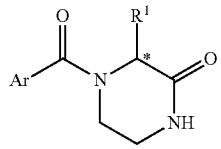
(C)

wherein * and the solid line extending from R¹ signify individual enantiomers, excluding racemic mixtures thereof;

b) converting the compound of Formula C with a tri(C1-C2 alkyl)oxonium salt, a (C1-C2)alkylsulfate, a (C1-C2)chloroformate or PCl₅/POCl₃/(C1-C2)hydroxyalkyl, so as to obtain a compound of Formula D:

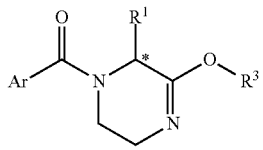
(D)

wherein Ar and R¹ are as defined above, and R³ is C1-C2 alkyl; and wherein * and the solid line extending from R¹ signify individual enantiomers, excluding racemic mixtures thereof;
in the presence of a base; and c) reacting the compound of Formula D with a compound of Formula E

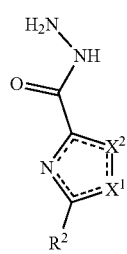
(E)

or a salt or solvate thereof, wherein X¹, X² and R² are as defined above;
so as to obtain a compound of Formula I or a solvate thereof.

2. The process according to claim 1 proceeding with the retention of stereochemistry with respect to the starting material.

3. The process according to claim 1, wherein the reaction of each step is carried out at room temperature.

4. The process according to claim 1, wherein the amide coupling reaction of step a) is carried out in an organic solvent at a temperature equal to or below boiling point of the organic solvent.

5. The process according to claim 1, wherein the process does not use any protecting group.

6. The process according to claim 1, wherein the base in step b) is selected from the group consisting of sodium carbonate, sodium bicarbonate, potassium carbonate and cesium carbonate.

7. The process according to claim 1, wherein the compound of Formula I is the (R)-enantiomer.

8. The process according to claim 1, wherein the compound of Formula I is

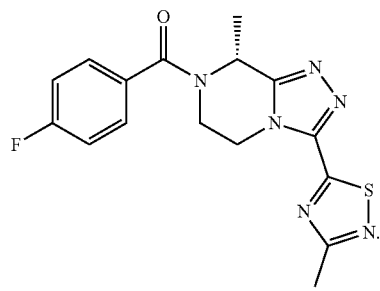 [SMILES: Cc1nsc(-c2nnc3n2CCN(C(=O)c2ccc(F)cc2)[C@@H]3C)n1]

9. The process according to claim 1, wherein the compound of Formula I is

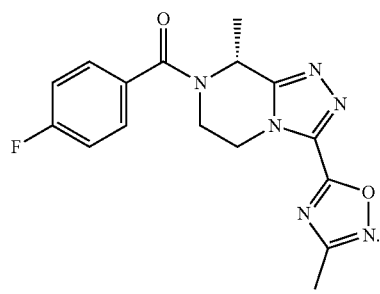 [SMILES: Cc1noc(-c2nnc3n2CCN(C(=O)c2ccc(F)cc2)[C@@H]3C)n1]

10. The process of claim 1, wherein the reaction of step b) is carried out in an organic solvent at a temperature equal to or below boiling point of the organic solvent.

11. The process of claim 1, wherein the reactions of steps a) and b) are carried out in dichloromethane.

12. The process of claim 11, wherein the reactions of steps a) and b) are carried out at room temperature.

13. The process of claim 1, wherein the reaction of step c) is carried out at a temperature between 50 ° C. and 135 ° C.

14. The process of claim 1, wherein the reaction of step c) is carried out at a temperature between 50 ° C. and 90 ° C.

* * * * *